(12) United States Patent
Hye-Ok et al.

(10) Patent No.: US 8,414,959 B2
(45) Date of Patent: *Apr. 9, 2013

(54) METHOD OF CONTACT COATING A MICRONEEDLE ARRAY

(75) Inventors: Choi Hye-Ok, Woodbury, MN (US); Gordon P. Knutson, Beldenville, WI (US); Moses M. David, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/290,610

(22) Filed: Nov. 7, 2011

(65) Prior Publication Data

US 2012/0114857 A1   May 10, 2012

Related U.S. Application Data

(63) Continuation of application No. 11/718,474, filed as application No. PCT/US2005/041993 on Nov. 18, 2005, now Pat. No. 8,057, 842.

(60) Provisional application No. 60/629,187, filed on Nov. 18, 2004.

(51) Int. Cl.
*A61M 3/00* (2006.01)
*A61M 37/00* (2006.01)
*A61M 5/32* (2006.01)
*B05C 1/00* (2006.01)
*B05C 1/14* (2006.01)

(52) U.S. Cl. ......... 427/2.28; 427/2.12; 427/2.3; 604/46; 604/239; 604/272

(58) Field of Classification Search .......... 427/2.1–2.31; 604/46, 239, 272, 21, 22
See application file for complete search history.

(56) References Cited

U.S. PATENT DOCUMENTS

| 2,619,962 A | 12/1952 | Rosenthal |
| 3,072,122 A | 1/1963 | Rosenthal |

(Continued)

FOREIGN PATENT DOCUMENTS

| WO | WO 96/10630 | 4/1996 |
| WO | WO 00/74766 | 12/2000 |

(Continued)

OTHER PUBLICATIONS

Tan et al. "Cells lying on a bed of microneedles: an approach to isolate mechanical force" Proc. National Acad. Sci. USA 100: 1484-1489, 2003.*

(Continued)

*Primary Examiner* — Timothy Meeks
*Assistant Examiner* — Cachet Sellman

(57) ABSTRACT

A method of coating a microneedle array by applying a coating fluid using a flexible film in a brush-like manner. A method of coating a microneedle array comprising: providing a microneedle array having a substrate and a plurality of microneedles; providing a flexible film; providing a coating solution comprising a carrier fluid and a coating material; applying the coating solution onto a first major surface of the flexible film; performing a transfer step of bringing the first major surface of the flexible film into contact with the microneedles and removing the flexible film from contact with the microneedles; and allowing the carrier fluid to evaporate.

29 Claims, 16 Drawing Sheets

U.S. PATENT DOCUMENTS

| | | | |
|---|---|---|---|
| 3,136,314 A | 6/1964 | Kravitz | |
| RE25,637 E | 9/1964 | Kravitz et al. | |
| 3,221,740 A | 12/1965 | Rosenthal | |
| 3,466,131 A | 9/1969 | Arcudi | |
| 3,470,011 A * | 9/1969 | Uhl et al. | 427/2.12 |
| 3,675,766 A | 7/1972 | Rosenthal | |
| 3,678,150 A | 7/1972 | Szumski et al. | |
| 3,688,764 A | 9/1972 | Reed et al. | |
| 3,964,482 A | 6/1976 | Gerstel et al. | |
| 4,473,083 A | 9/1984 | Maganias | |
| 4,474,751 A | 10/1984 | Haslam et al. | |
| 4,921,475 A | 5/1990 | Sibalis | |
| 5,192,535 A | 3/1993 | Davis et al. | |
| 5,250,023 A | 10/1993 | Lee et al. | |
| 5,279,544 A | 1/1994 | Gross et al. | |
| 5,340,572 A | 8/1994 | Patel et al. | |
| 5,402,798 A | 4/1995 | Swierczek et al. | |
| 5,440,446 A | 8/1995 | Shaw et al. | |
| 5,611,806 A | 3/1997 | Jang | |
| 5,879,326 A | 3/1999 | Godshall et al. | |
| 5,983,136 A | 11/1999 | Kamen | |
| 6,050,988 A | 4/2000 | Zuck et al. | |
| 6,091,975 A | 7/2000 | Daddona et al. | |
| 6,132,755 A | 10/2000 | Eicher et al. | |
| 6,219,574 B1 | 4/2001 | Cormier et al. | |
| 6,256,533 B1 | 7/2001 | Yuzhakov et al. | |
| 6,312,612 B1 | 11/2001 | Sherman et al. | |
| 6,322,808 B1 | 11/2001 | Trautman et al. | |
| 6,334,856 B1 | 1/2002 | Allen et al. | |
| 6,440,096 B1 | 8/2002 | Lastovich et al. | |
| 6,451,240 B1 * | 9/2002 | Sherman et al. | 264/504 |
| 6,454,755 B1 | 9/2002 | Godshall | |
| 6,503,231 B1 | 1/2003 | Prausnitz et al. | |
| 6,532,386 B2 | 3/2003 | Sun et al. | |
| 6,537,242 B1 | 3/2003 | Palmer | |
| 6,547,755 B1 | 4/2003 | Lippe et al. | |
| 6,589,202 B1 | 7/2003 | Powell | |
| 6,591,124 B2 | 7/2003 | Sherman et al. | |
| 6,595,947 B1 | 7/2003 | Mikszta et al. | |
| 6,603,998 B1 | 8/2003 | King et al. | |
| 6,611,707 B1 | 8/2003 | Prausnitz et al. | |
| 6,623,457 B1 | 9/2003 | Rosenberg | |
| 6,656,147 B1 | 12/2003 | Gertsek et al. | |
| 6,689,100 B2 | 2/2004 | Connelly et al. | |
| 6,696,157 B1 * | 2/2004 | David et al. | 428/408 |
| 6,713,291 B2 | 3/2004 | King et al. | |
| 6,743,211 B1 | 6/2004 | Prausnitz et al. | |
| 6,797,276 B1 | 9/2004 | Glenn et al. | |
| 6,855,131 B2 | 2/2005 | Trautman et al. | |
| 6,881,203 B2 | 4/2005 | Delmore et al. | |
| 6,881,538 B1 | 4/2005 | Haddad et al. | |
| 6,908,453 B2 | 6/2005 | Fleming et al. | |
| 6,931,277 B1 | 8/2005 | Yuzhakov et al. | |
| 7,627,938 B2 * | 12/2009 | Kim et al. | 29/458 |
| 2001/0044606 A1 | 11/2001 | Inkpen et al. | |
| 2002/0082543 A1 | 6/2002 | Park et al. | |
| 2002/0091357 A1 | 7/2002 | Trautman et al. | |
| 2002/0095134 A1 | 7/2002 | Pettis et al. | |
| 2002/0102292 A1 | 8/2002 | Cormier et al. | |
| 2002/0128599 A1 * | 9/2002 | Cormier et al. | 604/116 |
| 2002/0132054 A1 * | 9/2002 | Trautman et al. | 427/372.2 |
| 2002/0138049 A1 | 9/2002 | Allen et al. | |
| 2002/0169416 A1 | 11/2002 | Gonnelli et al. | |
| 2002/0177839 A1 | 11/2002 | Cormier et al. | |
| 2002/0177858 A1 | 11/2002 | Sherman et al. | |
| 2002/0193729 A1 | 12/2002 | Cormier et al. | |
| 2002/0198509 A1 | 12/2002 | Mikszta et al. | |
| 2003/0036710 A1 | 2/2003 | Matriano et al. | |
| 2003/0045837 A1 | 3/2003 | Delmore et al. | |
| 2003/0083641 A1 | 5/2003 | Angel et al. | |
| 2003/0135161 A1 | 7/2003 | Fleming et al. | |
| 2003/0187394 A1 | 10/2003 | Wilkinson et al. | |
| 2003/0187395 A1 | 10/2003 | Gabel et al. | |
| 2003/0199812 A1 | 10/2003 | Rosenberg | |
| 2003/0208167 A1 | 11/2003 | Prausnitz et al. | |
| 2004/0039343 A1 | 2/2004 | Eppstein et al. | |
| 2004/0049150 A1 | 3/2004 | Dalton et al. | |
| 2004/0077994 A1 | 4/2004 | Lastovich et al. | |
| 2004/0106904 A1 | 6/2004 | Gonnelli et al. | |
| 2004/0138612 A1 | 7/2004 | Shermer et al. | |
| 2004/0176732 A1 | 9/2004 | Frazier et al. | |
| 2004/0265365 A1 * | 12/2004 | Daddona et al. | 424/449 |
| 2005/0025778 A1 | 2/2005 | Cormier et al. | |
| 2005/0027242 A1 | 2/2005 | Gabel et al. | |
| 2005/0049549 A1 | 3/2005 | Wong et al. | |
| 2005/0065463 A1 | 3/2005 | Tobinaga et al. | |
| 2005/0065466 A1 | 3/2005 | Vedrine | |
| 2005/0065472 A1 | 3/2005 | Cindrich et al. | |
| 2005/0089554 A1 | 4/2005 | Cormier et al. | |
| 2005/0106226 A1 | 5/2005 | Cormier et al. | |
| 2005/0106227 A1 | 5/2005 | Zalipsky et al. | |
| 2005/0261631 A1 | 11/2005 | Clarke et al. | |

FOREIGN PATENT DOCUMENTS

| | | |
|---|---|---|
| WO | WO 01/36037 | 5/2001 |
| WO | WO 02/30281 | 4/2002 |
| WO | WO 02/085447 | 10/2002 |
| WO | WO 03/092785 | 11/2003 |
| WO | WO 2004-002566 | 1/2004 |
| WO | WO 2005/051455 | 6/2005 |
| WO | WO 2005/051476 | 6/2005 |
| WO | WO 2005/058393 | 6/2005 |
| WO | WO 2005/065765 | 7/2005 |
| WO | WO 2005/082596 | 9/2005 |

OTHER PUBLICATIONS

Xia et al. "Soft Lithography" Angew. Chem. Int. Ed. 1998, 37, pp. 550-575.*
Tan, J.L. et al.; "Cells lying on a bed of microneedles: An approach to isolate mechanical force"; Proc. Natl. Acad. Sci.USA; vol. 100, No. 4; (2003) pp. 1484-1489.
U.S. Appl. No. 60/578,651, filed Jun. 10, 2004, Frederickson et al.
Daddona Current Opinion in Drug Discovery and Development 1999 2(2);168-171.
Kaushik et al. Current Opinion in Drug Discovery and Development 1999 2(2);168-171.
Henry et al. J. Pharm.Sci., 1998, 87,8,922-925.
McAllister et al. (1) Annual Review of Biomedical Engineering, 2000, 2, 289-313.
McAllister et al. (2) Proceed. Int'l. Symp. Control Release of Bioactive Material, 26, (1999), CRS, 192-193.
Written Opinion of the ISA for Int'l Appln. No. PCT/US2005/041993, 10 pages.
Int'l Search Report for Int'l Appln. No. PCT/US2005/041993, 6 pages.

* cited by examiner

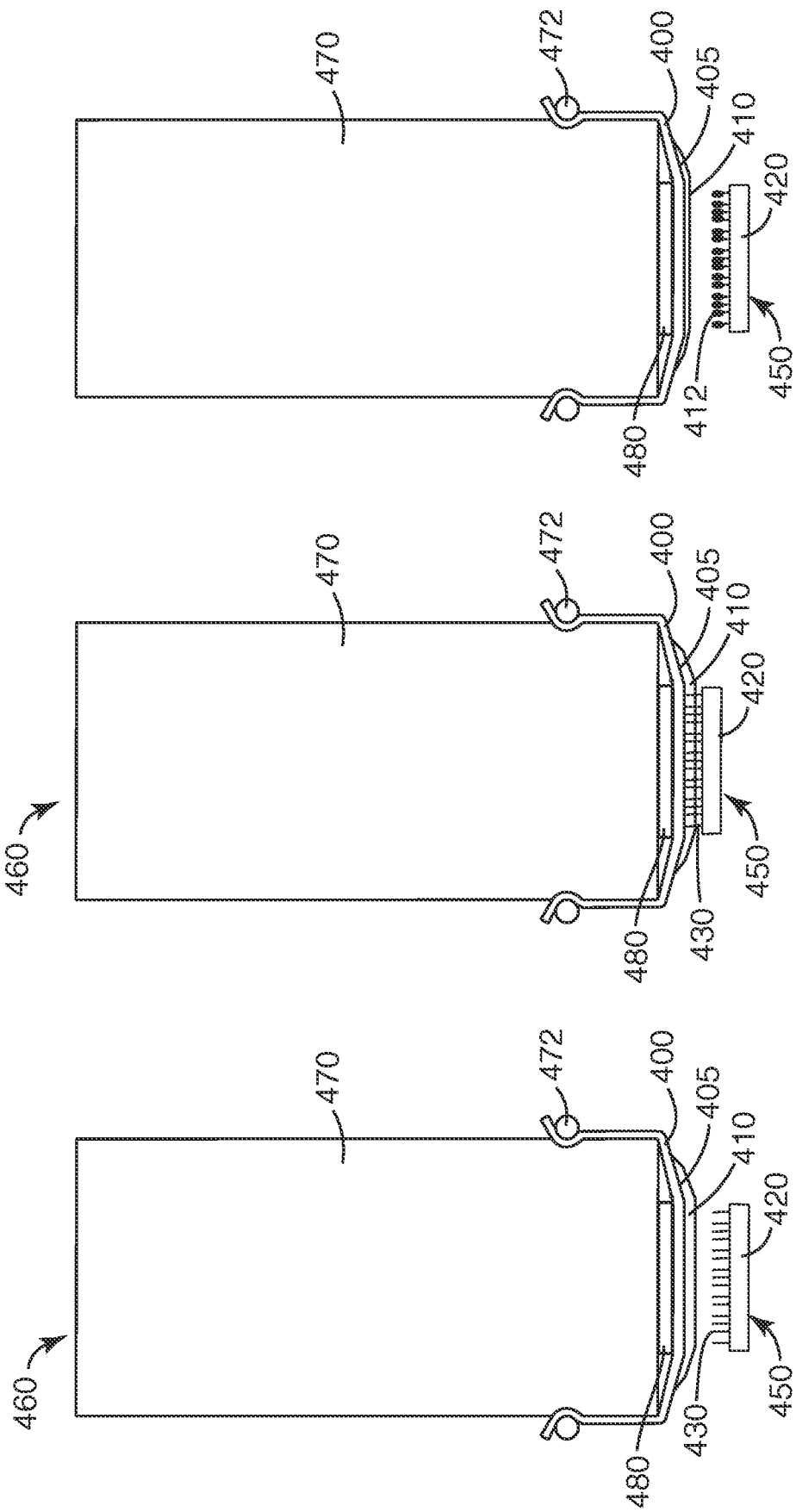

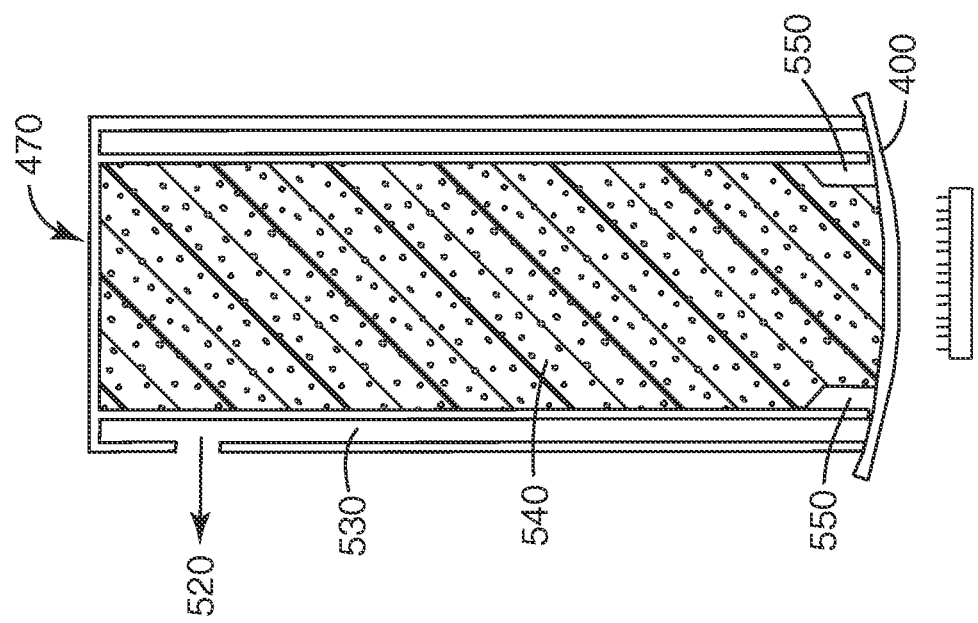
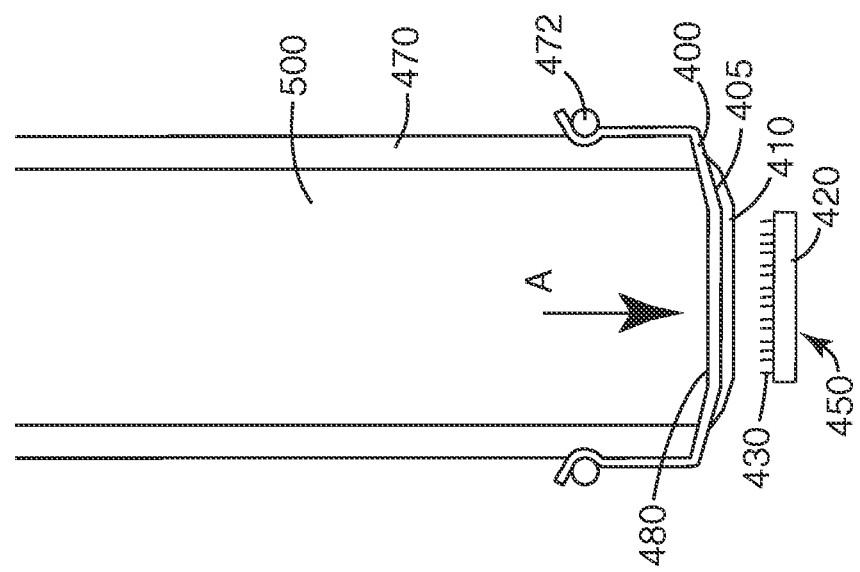

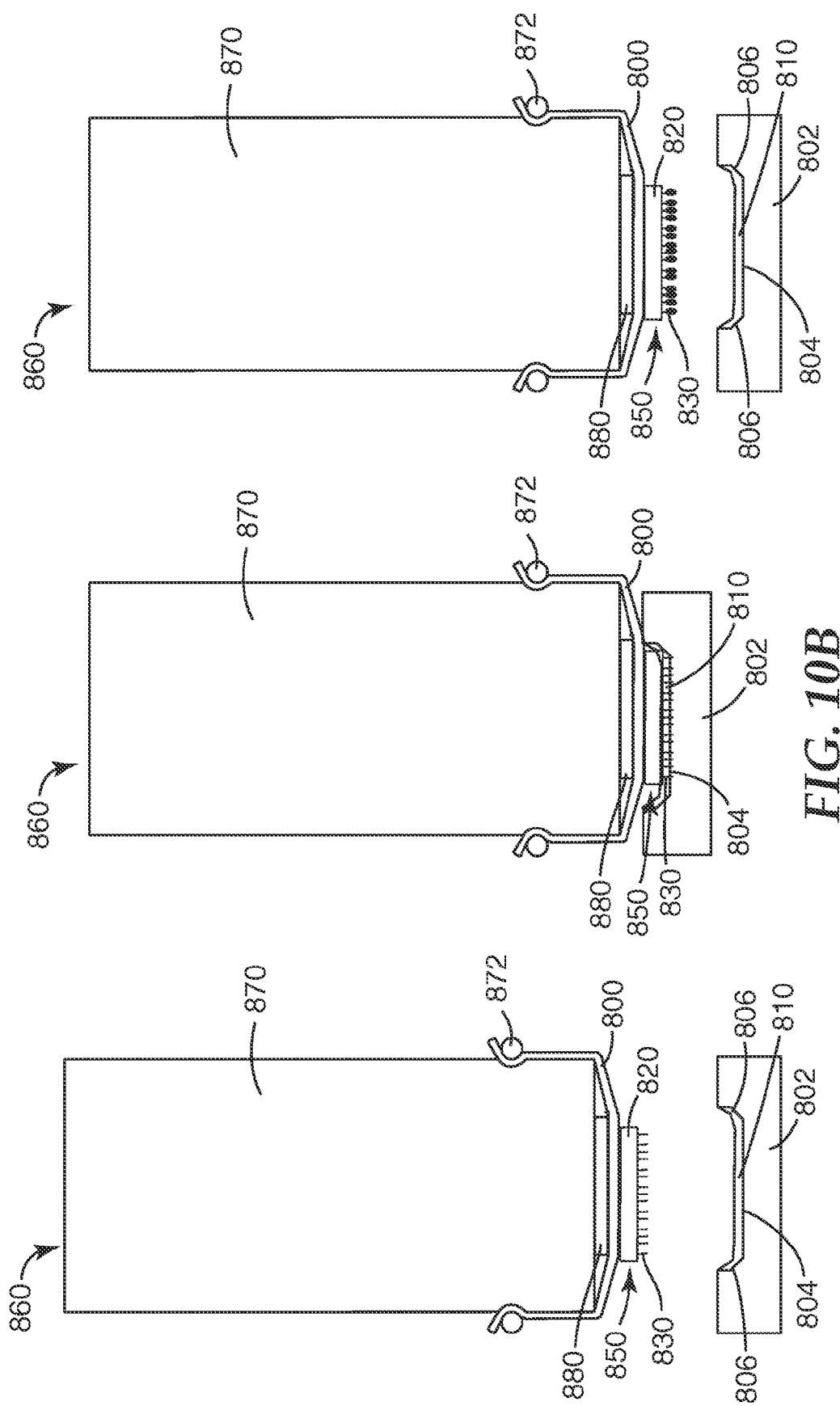

METHOD OF CONTACT COATING A MICRONEEDLE ARRAY

CROSS-REFERENCE TO RELATED APPLICATIONS

This application is a continuation of U.S. patent application Ser. No. 11/718,474, filed May 2, 2007, now U.S. Pat. No. 8,057,842, which is a national stage filing under 35 U.S.C. 371 of PCT/US2005/041993, filed Nov. 18, 2005, which claims priority to U.S. Provisional Application Ser. No. 60/629,187, filed on Nov. 18, 2004, which disclosure of which is incorporated herein by reference in their entirety.

FIELD

The present invention relates to methods of coating a microneedle array.

BACKGROUND

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Microneedle devices having a fluid reservoir and conduits through which a therapeutic substance may be delivered to the skin have been proposed, but there remain a number of difficulties with such systems, such as the ability to make very fine channels that can reliably be used for fluid flow.

Microneedle devices having a dried coating on the surface of a microneedle array have desirable features compared to fluid reservoir devices. The devices are generally simpler and can directly inject a therapeutic substance into the skin without the need for providing reliable control of fluid flow through very fine channels in the microneedle device.

SUMMARY OF THE INVENTION

The ability to provide a consistent coating in one or more desired locations on the microneedle array is an important feature for a microneedle device having a dried coating. Although there are numerous well known methods for providing dried coatings on generally flat surfaces, coating of a microneedle array provides a challenge due to the high surface irregularity inherent in any array design.

It has now been found that the location of a dried coating deposited from a coating fluid may be adjusted and controlled by bringing a microneedle array into direct contact with a coating substrate having an applied coating formulation. In one embodiment, the location of a dried coating deposited from a coating fluid may be adjusted and controlled by applying the coating fluid using a flexible film in a brush-like manner.

In a first aspect, the present invention provides a method of coating a microneedle array comprising providing a microneedle array having a substrate and a plurality of microneedles, providing a flexible film, providing a coating solution comprising a carrier fluid and a coating material, applying the coating solution onto a first major surface of the flexible film, performing a transfer step of bringing the first major surface of the flexible film into contact with the microneedles and removing the flexible film from contact with the microneedles; and allowing the carrier fluid to evaporate.

In a second aspect, the present invention provides a method of coating a microneedle array comprising providing a microneedle array having a substrate and a plurality of microneedles. A coating solution comprising a carrier fluid and a coating material is provided and applied onto a first major surface of a coating substrate to form a layer of applied coating solution having a thickness equal to or less than the height of at least one of the microneedles. A coating apparatus is provided comprising a coating substrate and a supporting member for the microneedle array, wherein at least one of the coating substrate and the microneedle array is flexibly mounted within the coating apparatus. A transfer step is performed by bringing the first major surface of the coating substrate into contact with the microneedles and removing the coating substrate from contact with the microneedles, thereby transferring at least a portion of the coating solution to the microneedle array. The transferred carrier fluid is allowed to evaporate.

As used herein, certain terms will be understood to have the meaning set forth below:

"Array" refers to the medical devices described herein that include one or more structures capable of piercing the stratum corneum to facilitate the transdermal delivery of therapeutic agents or the sampling of fluids through or to the skin.

"Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum.

The features and advantages of the present invention will be understood upon consideration of the detailed description of the preferred embodiment as well as the appended claims. These and other features and advantages of the invention may be described below in connection with various illustrative embodiments of the invention. The above summary of the present invention is not intended to describe each disclosed embodiment or every implementation of the present invention. The Figures and the detailed description which follow more particularly exemplify illustrative embodiments.

BRIEF DESCRIPTION OF THE DRAWINGS

Preferred embodiments of the invention will now be described in greater detail below with reference to the attached drawings, wherein:

FIGS. 8A, 8B, and 8C are schematic cross-sectional views of the transfer step of another embodiment of the present invention.

FIGS. 9A to 9E are schematic cross-sectional views of alternative embodiments for supporting a flexible film coating substrate.

FIGS. 10A, 10B, and 10C are schematic cross-sectional views of the transfer step of another embodiment of the present invention.

DETAILED DESCRIPTION

Figure 1:
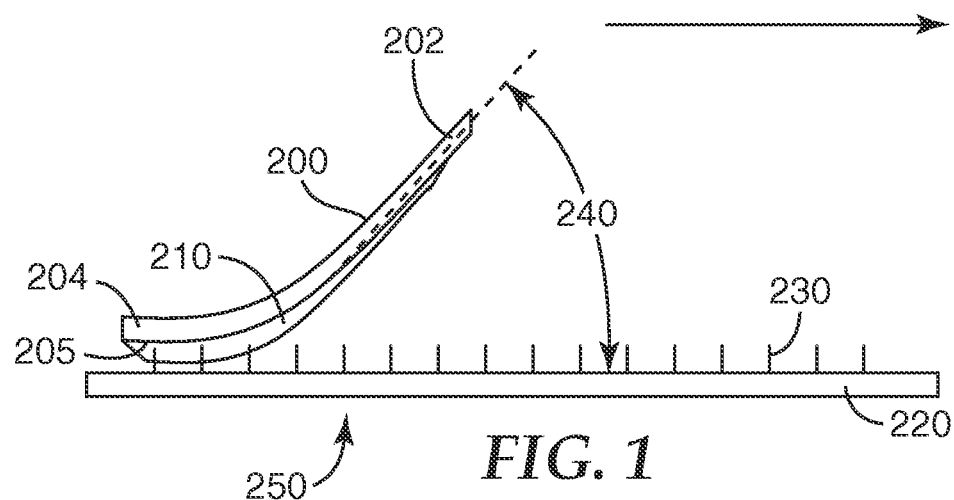
FIG. 1 is a schematic cross-sectional view of one embodiment of the present invention during the transfer step.

One aspect of the method of the present invention is shown in FIG. 1. A microneedle array 250 is provided having a substrate 220 and microneedles 230 extending from the substrate. A coating solution 210 has been applied to the first major surface 205 of a flexible film 200 prior to the illustrated transfer step. The coating solution 210 comprises a carrier fluid and a coating material. The flexible film 200 serves as a flexible coating substrate and has a leading edge 202 that is connected to a source of movement and a trailing edge 204 that is brought into contact with the microneedles 230 during the transfer step. As shown, the flexible film 200 with coating solution 210 is oriented so that the coating solution 210 contacts the microneedles 230 when the film 200 is brought into contact with the tips of the microneedles. The film is moved in a linear direction across the array in the direction of the arrow shown in FIG. 1. After the film has been moved across the area of the array that is desired to be coated, it is then removed and the carrier fluid is allowed to evaporate, thereby leaving dried coating material on the microneedle array 250. The leading edge 202 portion of the flexible film 200 is oriented at a flexure angle, 240, with respect to the substrate 220 as shown.

In one embodiment the microneedle array is oriented so that the microneedles are facing upward and the coating solution on the flexible film is facing downwards when it is brought into contact with the microneedles. The terms upwards and downwards refer to orientation with respect to gravity. That is, the force of gravity will cause the flexible film to rest on the microneedle array when the flexible film is facing downwards. This orientation need not be precisely aligned with respect to gravity, but need only be sufficient such that the flexible film may rest on the microneedle array due to the force of gravity alone. In one embodiment, the microneedle array is oriented so that it is perpendicular to the force of gravity. In one aspect, an optional supporting member may be attached to the flexible film, and in particular to the upper surface of the trailing edge of the film, to assist the contact between coating solution and microneedles.

Although the flexible film is shown moving in a linear direction across the microneedle array during the transfer step, it may be moved in a non-linear fashion, such as in a curved or stepwise motion, to adjust the amount and location of deposited coating material or to simplify the manufacturing process.

Figure 3B:
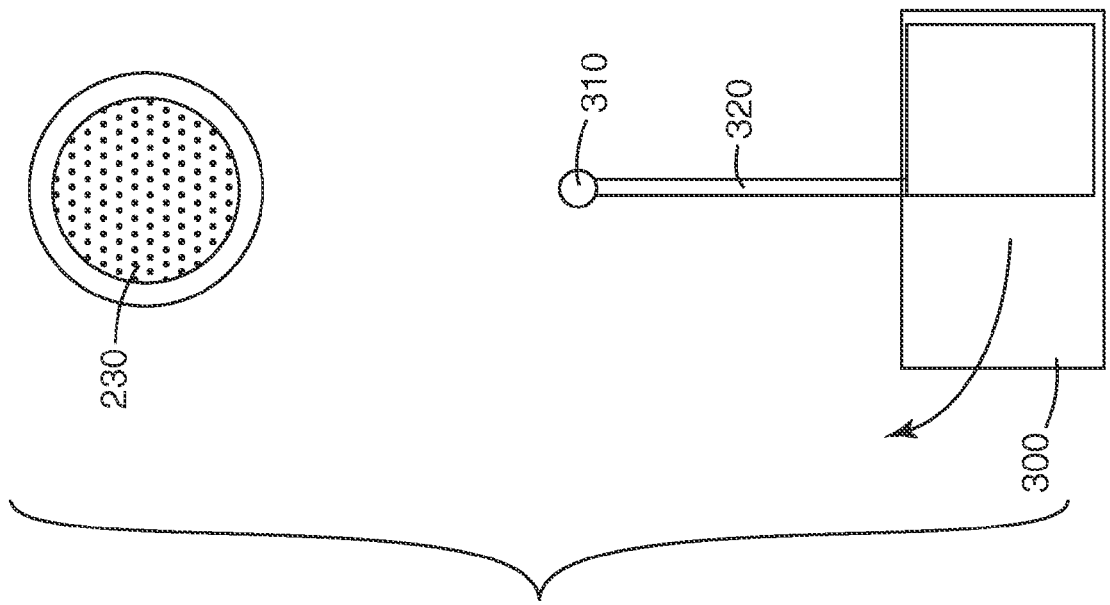
FIGS. 3A and 3B are schematic plan views of another embodiment of the present invention.
Figure 3A:
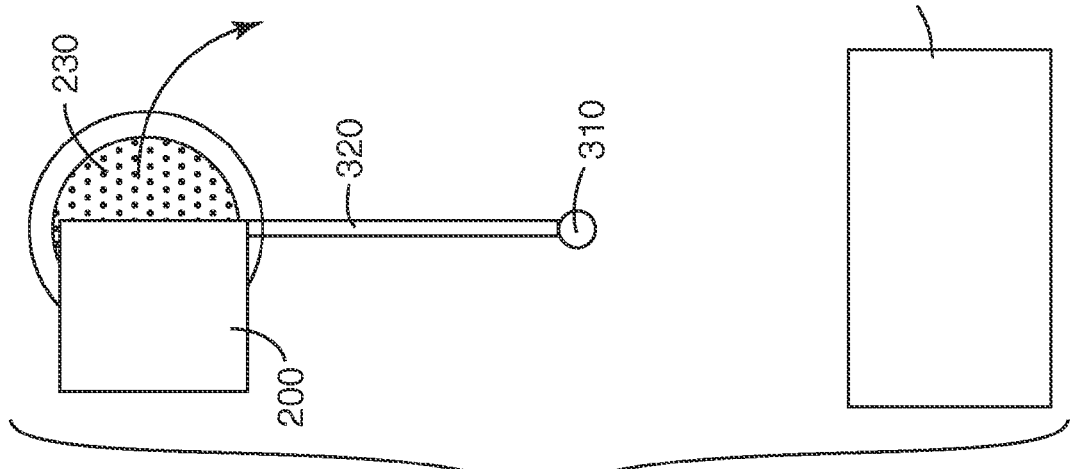

In one embodiment, a coating apparatus is used wherein the flexible film 200 may be mounted on a rotational arm 320 such that it contacts the microneedles 230 during one part of a rotation (shown in FIG. 3A) and such that additional coating solution is added to the film 200 from a fluid reservoir 300 during another part of the rotation (shown in FIG. 3B). The amount of coating solution added to the flexible film from the fluid reservoir is desirably about the same as the amount of coating material deposited on the microneedles. In another aspect, a reservoir may be in direct fluid communication and/or contact with the flexible film throughout the entire coating cycle so as to supply coating solution to the film continuously or on-demand, as desired. The flexible film 200 as shown in FIGS. 1 and 3 is flexibly mounted in the coating apparatus. One edge of the flexible film is rigidly held on the rotational arm, thus leaving the other (trailing) edge of the film to freely flex as it contacts the microneedle array (i.e., the trailing edge of the film is flexibly mounted). The trailing edge will generally be aligned so that it moves in a plane parallel to and below a plane formed by the tips of the microneedle array, so that it will interfere with the array and flex when it comes into contact with the array (as shown in FIG. 1). This distance between the plane of motion of the trailing edge and the a plane formed by the tips of the microneedle array is referred to as the edge-array interference and is typically between about 50 and 1000 μm, sometimes between about 200 and about 500 μm.

Figure 2A:
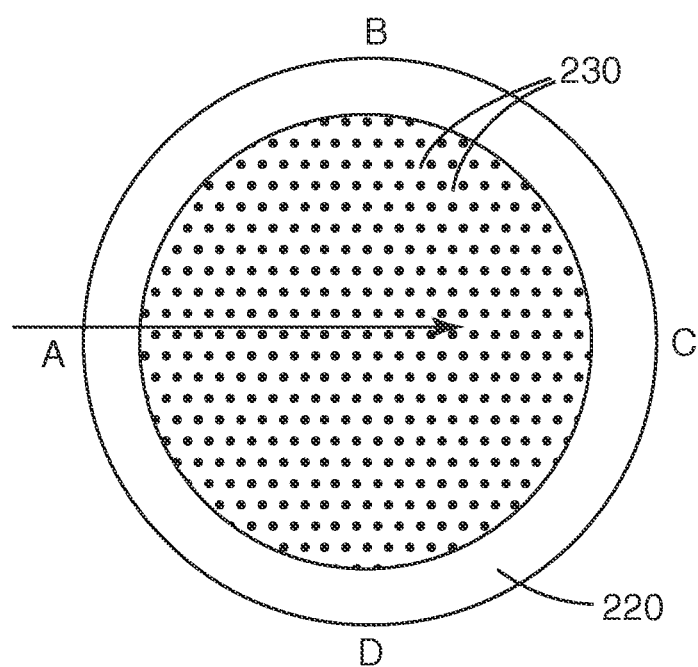
FIGS. 2A and 2B are a schematic plan and cross-sectional view, respectively, of the transfer step of one embodiment of the present invention.
Figure 2B:
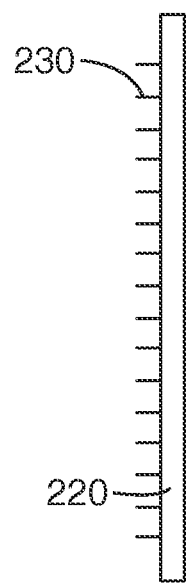
Figure 2C:
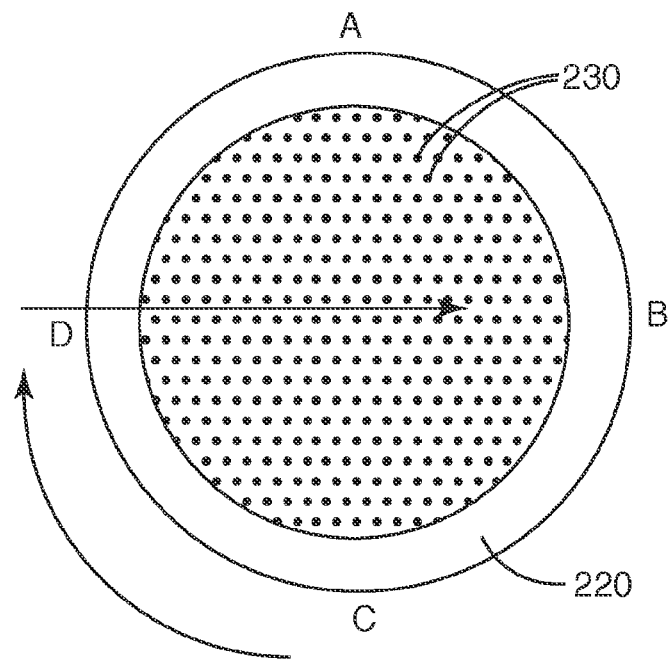
FIGS. 2C and 2D are a schematic plan and cross-sectional view, respectively, where the microneedle array has been rotated in between multiple transfer steps.
Figure 2D:
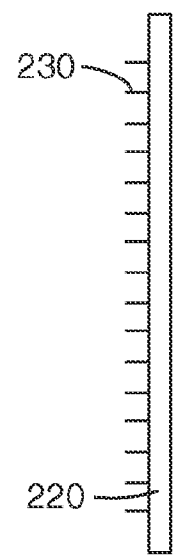

The transfer step shown may be repeated one or more times in order to transfer additional coating material to the microneedle array 250. The microneedle array may be moved with respect to the direction of motion of the film movement in between the repeated steps. This is shown in FIGS. 2A-2D where the microneedle array is shown with directional indicators (A, B, C, D) to indicate orientation of the array. A first transfer step is shown in FIGS. 2A and 2B where the flexible film is moved in the direction from A to C. The microneedle array is then rotated approximately 90° prior to the transfer step shown in FIGS. 2C and 2D where the flexible film is moved in the direction from D to B. This procedure may be repeated so that a subsequent step, for instance, would have the flexible film moving in the direction from C to A. Of course, it is equally valid to hold the microneedle array fixed and change the direction of motion of the flexible film, as it is the relative motion between the two that is of importance. Any combination of transfer steps and rotational movements are suitable. Although the rotation shown in FIG. 2C is approximately 90°, rotational movements may be of any other amount. In a preferred embodiment transfer steps and rotational movements are alternated on a one-to-one basis. In one embodiment the size of each rotational movement is selected so as to be evenly divisible into 360° (e.g., 30°, 45°, 60°, 90°, 120°, 180°, etc.) and more preferably so that the total rotational movement sums to 360° less the size of a single rotational movement. For instance, using the orientational markings shown in FIG. 2A, the following sequence may be used where the transfer steps all occur in the direction shown by the arrow: a transfer step in the direction A to C, a 90° clockwise rotational movement of the microneedle array, a transfer step in the direction D to B, a 90° clockwise rotational movement of the microneedle array, a transfer step in the direction C to A, a 90° clockwise rotational movement of the microneedle array, a transfer step in the direction B to D.

FIGS. 3A and 3B show additional detail of a coating apparatus suitable for performing the transfer step. A microneedle array with microneedles 230 is shown held in a stationary position. A pivot axis 310 and pivot arm 320 hold a flexible film 200 carrying coating material (not shown) which is advancing across the microneedles 230 (shown in FIG. 3A) and thereby transferring coating material from the flexible film 200 to the microneedles 230. The film is then rotated 180 degrees (shown in FIG. 3B) and passed across a reservoir 300 of coating material. The flexible film 200 is oriented so that it picks up additional coating material from the reservoir 300. These steps may be repeated, that is, the film with coating material may again be rotated to alternately contact the microneedles (and deposit coating material) and contact the reservoir (to pick up additional coating material).

Figure 7C:
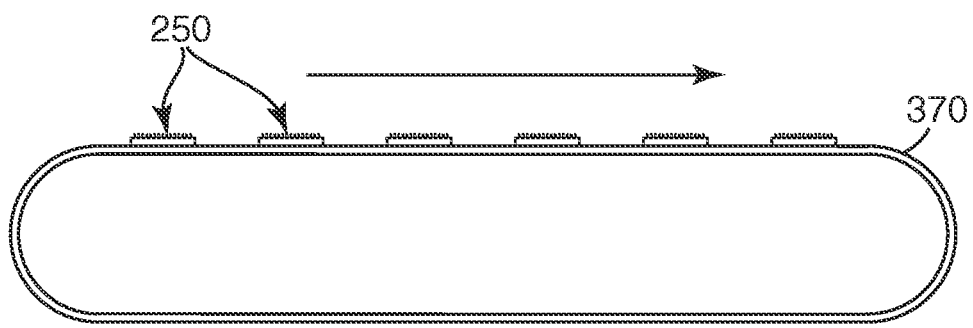
FIGS. 7B and 7C are schematic cross-sectional views of a portion of a coating apparatus in various embodiments of the present invention.
Figure 6A:
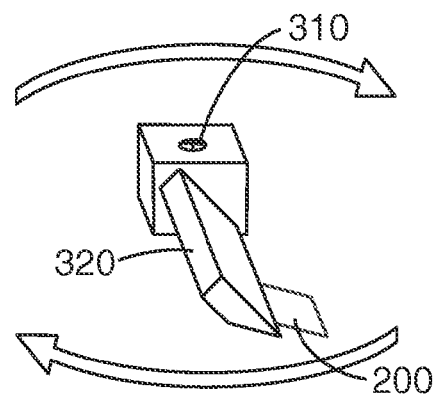
FIGS. 6A and 6B are schematic perspective views of a portion of a coating apparatus in various embodiments of the present invention.
Figure 6B:
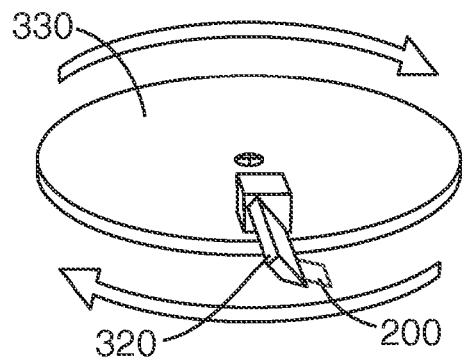
Figure 6C:
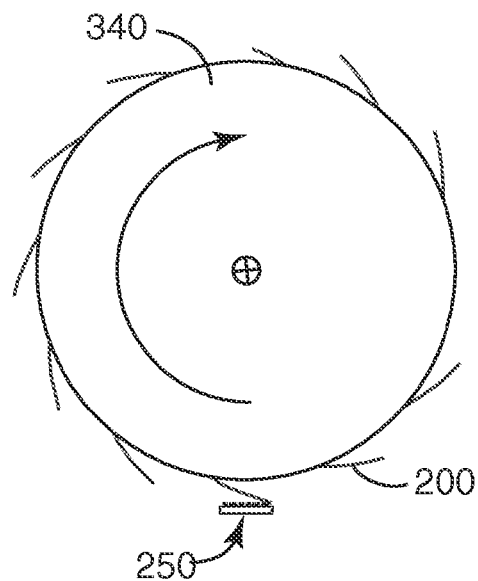
FIG. 6C is a schematic cross-sectional view of a portion of another embodiment of a coating apparatus.
Figure 7A:
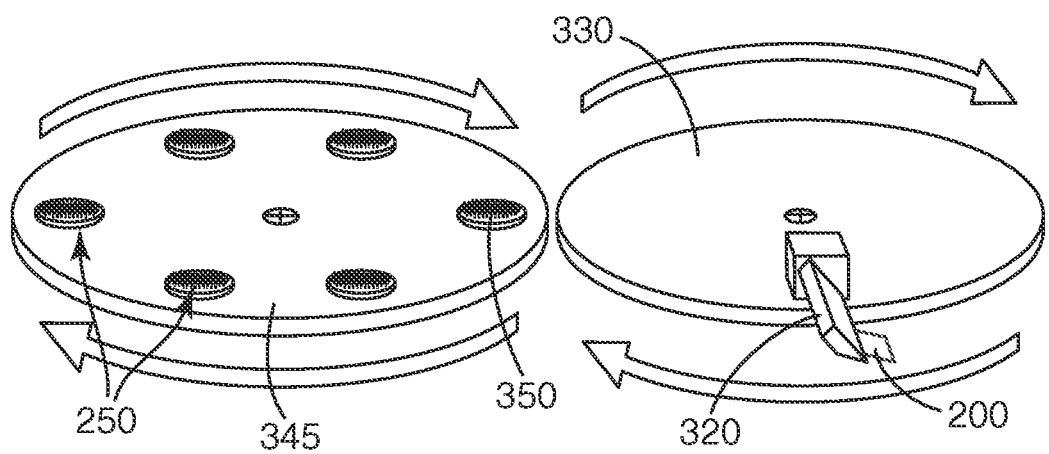
FIG. 7A is a schematic perspective view of a portion of a coating apparatus in one embodiment of the present invention.
Figure 7B:
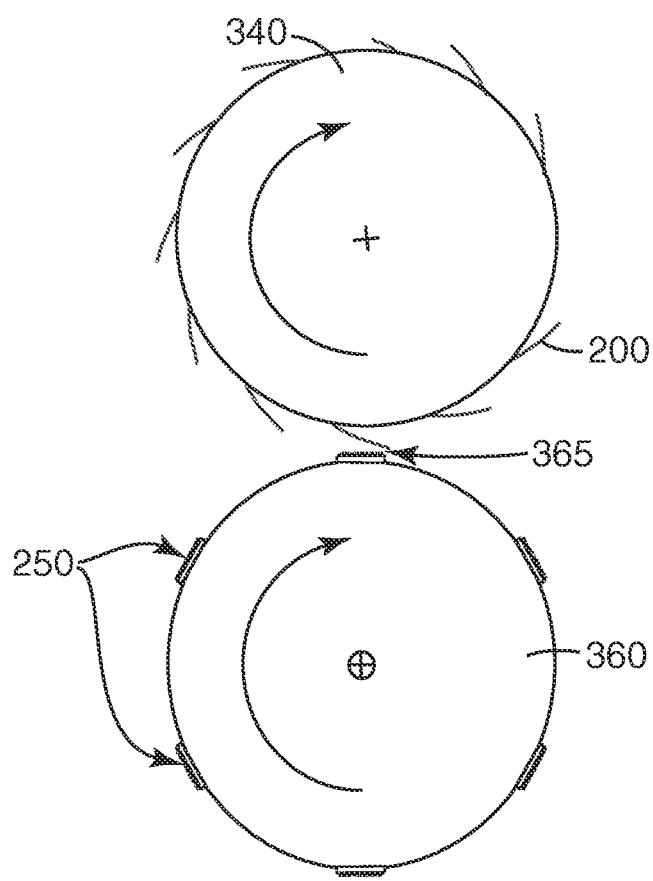

Any combination of rotational and/or translational motion of the flexible film may be employed to both apply the coating solution onto the film and to effect the transfer step. FIG. 6A shows a perspective view of a coating apparatus with a pivot axis 310 and a pivot arm 320 holding a flexible film 200 with the large arrows indicating the direction of rotation of the film in a horizontal plane containing the microneedle array (not shown). Alternatively, the pivot arm 320 may be attached to a rotating disk 330 as shown in FIG. 6B. In still another embodiment (FIG. 6C), the film 200 may be directly attached to a roll 340 that rotates in a plane perpendicular to the microneedle array 250. Likewise, any combination of rotational and/or translational motion of the microneedle array 250 may be employed to bring the microneedles into contact with the flexible film 200. FIG. 7A shows a perspective view of microneedle arrays 250 held on a rotating disk 345 that is employed to advance the arrays 250 to a position 350 where they may be contacted by the flexible film 200 (at a point where the flexible film is advanced another 90 degrees from the orientation shown in the figure). Alternatively (FIG. 7B), the arrays may be held on a roll 360 that rotates in a plane perpendicular to the plane of the microneedle array. As shown, the roll 360 brings the arrays 250 to a position 365 where they may be contacted by the flexible film 200. In still another embodiment (FIG. 7C) the arrays 250 may be moved in a linear fashion by a conveyer belt 370 so as to advance the arrays to a position where they may be contacted by the flexible film 200. The arrays may also be rotated about a central axis as described above. It should be understood that the foregoing embodiments are merely exemplary and any suitable conventional means of motion may be used to bring the flexible film into contact with the microneedles.

In one embodiment where repeated transfer steps are performed, the carrier fluid may be allowed to substantially completely evaporate following a transfer step and before a subsequent transfer step. In another embodiment, the temporal spacing of subsequent transfer steps may be selected so that some or all of the carrier fluid deposited in previous transfer steps remains on the microneedles.

The desired flexure angle may depend on a number of factors, including the type of material and thickness of the flexible film, the shape and type of material of the microneedle array, the type of coating solution, the amount of coating solution to be applied, and the desired location of the subsequent dried coating on the array. Although any flexure angle is suitable, the flexure angle is typically between 0° and 90°, often between 5° and 30°, and sometimes between 5° and 15°. The flexure angle may be held at a single fixed value during one or more transfer steps or it may be varied during a transfer step or varied from one transfer step to another.

The rate at which the flexible film is moved (also referred to as the 'transfer rate') in relation to the microneedle array may vary, but is typically between 0.01 m/s and 10 m/s, often between 0.05 m/s and 1 m/s, and sometimes between 0.1 m/s and 0.5 m/s. The transfer rate may be held at a single fixed value during one or more transfer steps or it may be varied during a transfer step or varied from one transfer step to another.

The amount of the coating solution applied to the flexible film may be adjusted depending on the desired amount of coating material to be applied and the desired location of the subsequent dried coating on the array. The coating solution will typically form a coating layer having a thickness that is typically equal to or less than the height of the microneedles and is often between 10 and 90% of the height of the microneedles and sometimes between 30 and 50% of the height of the microneedles. In some embodiments the coating layer will have a thickness of between 20 and 200 microns and sometimes between 20 and 50 microns. The coating solution may be applied to the flexible film by any of a number of conventional methods used to coat flat substrates. It may be desirable to use a coating method that provides a relatively even coating thickness across the area of the flexible film that comes in contact with the microneedles during the transfer step. Alternatively, if a coating layer of uneven thickness is applied to the flexible film, then it may be desirable to include a step to make the thickness more even (such as doctoring) prior to the transfer step. The amount of coating solution transferred to the microneedles during a transfer step is typically more than 0.1 μL, often between 0.1 μL and 10 μL, and sometimes between 0.5 μL and 2 μL.

The flexible film (i.e., coating substrate) may be any suitable flexible material that can be contacted with the microneedle array without causing undue damage to the delicate microneedles. Typical films may be thin polymeric or paper films. Suitable examples of thin polymeric films include nylon, polyethylene, polypropylene, polyurethane, and polyethylene terephthalate. It may be desired to use a membrane material, such as a nylon filter having 0.20 or 0.45 micron pores. It may be desirable for any porous features in the flexible film surface to be smaller than the approximate size of the microneedle tips, so as to avoid any potential for mechanical interlocking between the microneedles and the coating substrate. The desired thickness of the film will depend on the material of the film and the type of microneedles, but is typically less than 250 microns, sometimes less than 100 microns, and may be less than 50 microns.

The area of the flexible film may vary depending on the size and shape of the microneedle array to be coated. In one embodiment, the area of the film may be sufficient to coat more than one microneedle array in a single transfer step. The flexible film may have any of a number of different shapes including, for example, a square, rectangle, circle, or oval.

In one embodiment, the shape of the flexible film is chosen so that it has a uniform trailing edge, such as, for example, a film in the shape of a square or rectangle. This may aid in providing a uniform coating across the width of the array. The area of a trailing edge of the film that comes in contact with the array will typically have a width similar to the widest dimension of the microneedle array to be coated and a length of between about 0.05 cm and 1.0 cm, often between about 0.05 cm and 0.5 cm, and sometimes between about 0.1 cm and 0.2 cm. In another embodiment, substantially the entire film area will come into contact with the array, in which case the film typically has an area of between about 0.2 and 1.5 times the area of the array, often between about 0.5 and 1.2 times the area of the array, and sometimes an area about 1.0 times the area of the array.

In one embodiment, the flexible film may be treated, such as with a chemical or physical surface treatment, in order to control or enhance the wetting properties of the coating solution on the coating substrate. For example, it may be desired to apply a hydrophilic surface treatment to all or part of the coating substrate to enhance the wetting properties of aqueous coating solutions. In one embodiment, a surface treatment may be applied such that only a portion of the leading edge of the flexible film is surface treated and substantially all of the trailing edge of the flexible film is surface treated. Such a differential treatment may aid in channeling coating solution from the leading edge to the trailing edge of the flexible film.

The coating solution comprises a carrier fluid or solvent and at least one dissolved or dispersed coating material that will ultimately become the dried coating on the microneedle array. The coating solution may comprise more than one dissolved coating material, more than one dispersed or suspended coating material, or a mixture of dissolved and dispersed coating materials. In one embodiment, the coating material may be a therapeutic agent. The carrier fluid or solvent should be selected such that it may dissolve or disperse the material intended for coating. Examples of suitable carrier fluids or solvents include water, ethanol, methanol, isopropanol, ethyl acetate, hexane, and heptane. The carrier fluid is evaporated after application to the microneedle array to leave dried coating material on the microneedle array. Evaporation may be allowed to take place at ambient conditions or may be adjusted by altering the temperature or pressure of the atmosphere surrounding the microneedle array. Evaporation conditions are desirably selected so as to avoid degradation of the coating material. The coating solution may contain additional excipients including, for example, viscosity modifiers, stabilizers, and other additives. Examples of suitable additional excipients include sucrose, ovalbumin, and hydroxyethyl cellulose.

Dried coating material is deposited on the microneedle array upon evaporation of the transferred coating solution. In one embodiment, the dried coating material is preferentially deposited on the microneedles. By preferentially deposited it is meant that the amount of dried coating per unit surface area will be greater on the microneedles than on the substrate. More preferably, the dried coating material is preferentially deposited on or near the tips of the microneedles. In some cases more than half of the dried coating material by weight is deposited on the microneedles. In some cases the dried coating preferentially resides on the upper half of the microneedles, that is, the portion of the microneedles away from the substrate. In one embodiment substantially no dried coating material is deposited on the substrate, that is, substantially all of the dried coating material is deposited on the microneedles. In one embodiment, substantially all of the dried coating material is deposited on the upper half of the microneedles. The thickness of the dried coating material may vary depending on the location on the microneedle array and the intended application use for the coated microneedle array. Typical dried coating thicknesses are less than 50 microns, often less than 20 microns and sometimes less than 10 microns. It may be desirable for the coating thickness to be smaller near the tip of the microneedle so as not to interfere with the ability of the microneedle to effectively pierce into the skin.

Figure 5:
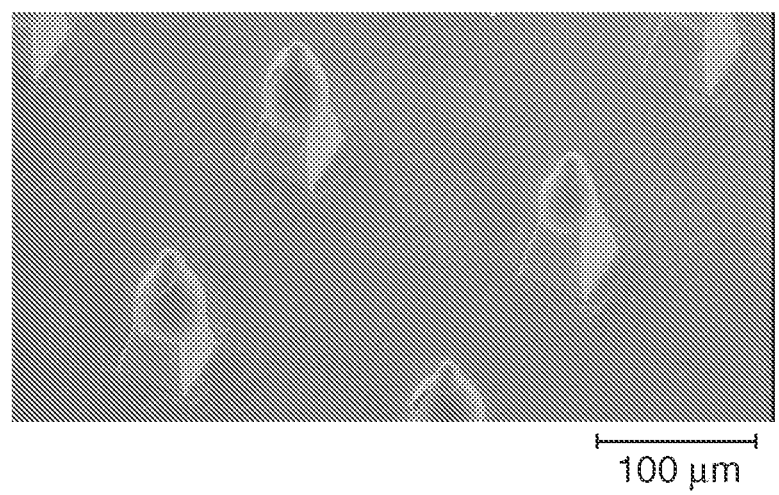
FIG. 5 is a scanning electron micrograph of a coated microneedle array.

FIG. 5 shows a scanning electron micrograph of a coated microneedle array where the coated material has formed a "teardrop" shape near the tip of the microneedle. This shape may be particularly desirable as it concentrates material near the tip of the microneedle, but does not appreciably alter the tip geometry, thus allowing for efficient piercing of the skin and delivery of coated material into the skin. The teardrop shape may be generally characterized by the maximum dimension of the dried coating when observed from above (i.e., looking down at the shaft of the needle towards the microneedle array substrate) and the height above the substrate where the maximum dimension of the dried coating occurs.

In one embodiment, the dried coating material may contain a pharmacological agent and the pharmacological agent is preferentially deposited on the microneedles. By preferentially deposited it is meant that the amount of pharmacological agent per unit surface area will be greater on the microneedles than on the substrate. More preferably, the pharmacological agent is preferentially deposited on or near the tips of the microneedles. In some cases more than half of the pharmacological agent by weight is deposited on the microneedles. In some cases the pharmacological agent preferentially resides on the upper half of the microneedles, that is, the portion of the microneedles away from the substrate. In one embodiment substantially no pharmacological agent is deposited on the substrate, that is, substantially all of the pharmacological agent is deposited on the microneedles. In one embodiment, substantially all of the pharmacological agent is deposited on the upper half of the microneedles.

Figure 4:
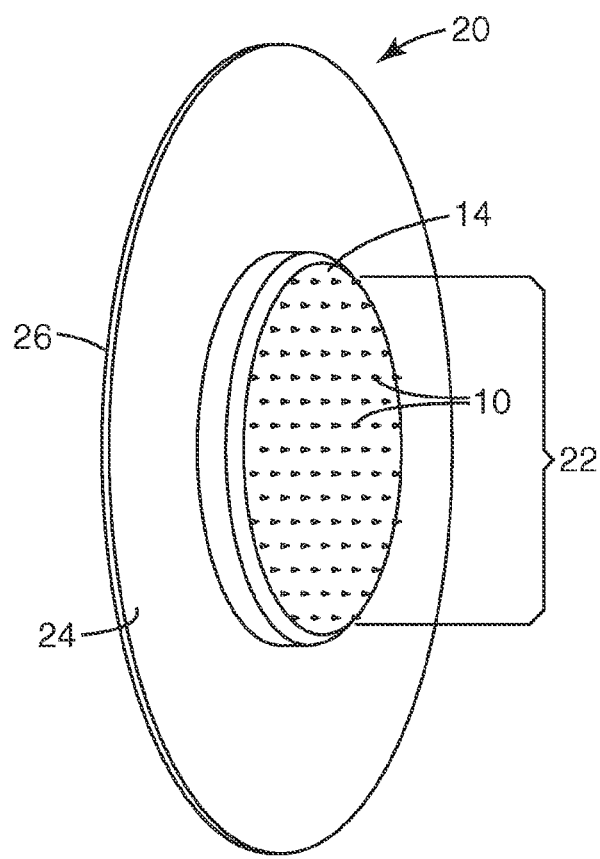
FIG. 4 is a schematic perspective view of patch microneedle device.

In one embodiment, the microneedle array shown in FIGS. 1 and 2 may be applied to a skin surface in the form of a patch shown in more detail in FIG. 4. FIG. 4 illustrates a microneedle device comprising a patch 20 in the form of a combination of an array 22, pressure sensitive adhesive 24 and backing 26. A portion of the array 22 is illustrated with microneedles 10 protruding from a microneedle substrate surface 14. The microneedles 10 may be arranged in any desired pattern or distributed over the microneedle substrate surface 14 randomly. As shown, the microneedles 10 are arranged in uniformly spaced rows. In one embodiment, arrays of the present invention have a distal-facing surface area of more than about 0.1 $cm^2$ and less than about 20 $cm^2$, preferably more than about 0.5 $cm^2$ and less than about 5 $cm^2$. In one embodiment (not shown), a portion of the substrate surface 14 of the patch 20 is non-patterned. In one embodiment the non-patterned surface has an area of more than about 1 percent and less than about 75 percent of the total area of the device surface that faces a skin surface of a patient. In one embodiment the non-patterned surface has an area of more than about 0.10 square inch (0.65 $cm^2$) to less than about 1 square inch (6.5 $cm^2$). In another embodiment (shown in FIG. 4), the microneedles are disposed over substantially the entire surface area of the array 22.

A second aspect of the method of the present invention is shown in FIG. 8A. A microneedle array 450 is provided having a substrate 420 and microneedles 430 extending from the substrate. A coating solution 410 has been applied to the first major surface 405 of a flexible film 400. The coating solution 410 comprises a carrier fluid and a coating material. The flexible film 400 serves as a flexible coating substrate and is flexibly mounted to a rod 470. The film 400 is part of a dauber assembly 460 and held in place with an attachment band 472. As shown, the flexible film 400 is supported by a pad 480 positioned between the rod 470 and the back of the flexible film 400, thus allowing flexural motion of the film 400.

The first major surface 405 of the flexible film 400 is brought into contact with the microneedles 430 during a transfer step as shown in FIG. 8B, thereby bringing the coating solution 410 into contact with the microneedles 430. The flexible film 400 is then removed from contact with the microneedles 430 as shown in FIG. 8C, thereby transferring at least a portion of the coating solution 410 to the microneedle array 450. The transferred carrier fluid is then allowed to evaporate, thereby leaving a dried coating 412 on the microneedle array 450.

The flexible film 400 may be brought into contact with the microneedles 430 by moving one or both of the dauber assembly 460 and/or the microneedle array 450 towards each other. In one embodiment, the microneedle array 450 is held fixed in place during the transfer step and the dauber assembly 460 is moved in a direction generally perpendicular to the plane of the microneedle array. The plane of the microneedle array should be understood to be a plane generally defined by the tips of the microneedles. As shown in FIG. 8A, such a plane is parallel to the substrate 420 of the microneedle array 450. It should be understood that the tips of the microneedle array need not lie exactly within a single plane, but that a single plane will be at least approximately congruent with the tips of the microneedles.

Figure 9E:
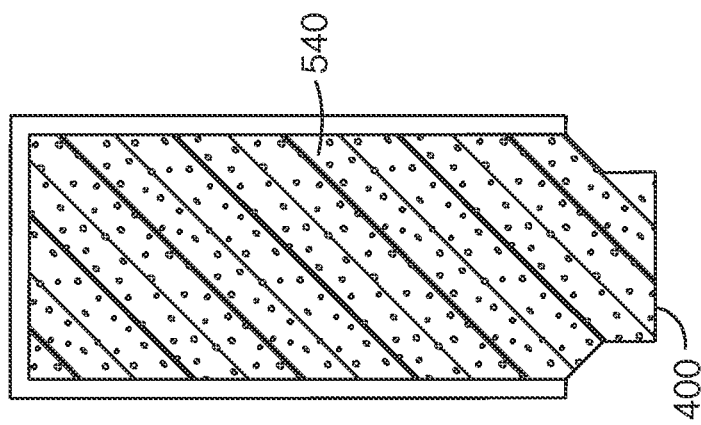
Figure 9D:
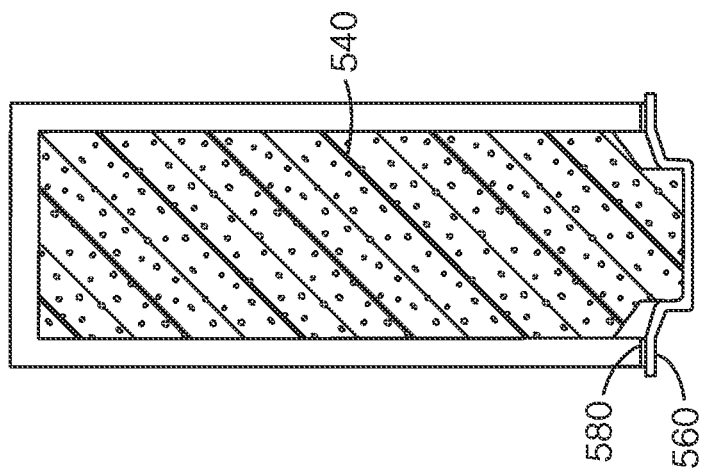
Figure 9C:
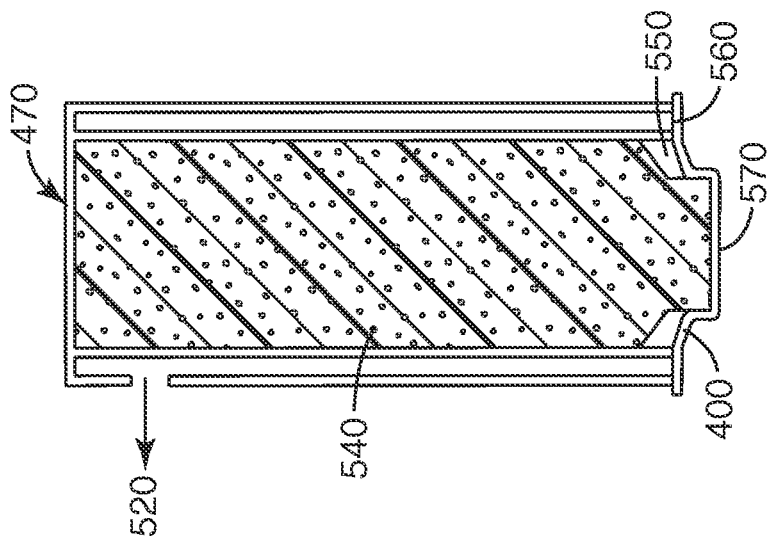

The flexible film 400 may be supported and attached to the dauber assembly 460 by any suitable means. FIG. 9A shows the film 400 supported by a column of air or other fluid 500 that is held under pressure within the rod 470, which is hollow in this embodiment. The air or fluid 500 applies pressure in the direction of the arrow A against the film 400. FIG. 9B shows the film attached to the dauber assembly 460 by means of a vacuum 520 that is drawn through an outer chamber 530 of the rod 470. As shown, the rod is filled with a foam 540 that supports the film 400. Recessed areas 550 are provided within the supporting foam 540, which may facilitate compression of the foam during the transfer step. An optional supporting plate, such as a thin metal piece may be placed between the film 400 and the foam 540. FIG. 9C is a variation of the embodiment shown in FIG. 9B wherein the film 400 is thermoformed so as to provide a contoured surface. The outer edge 560 of the film 400 serves to provide attachment to the rod 470 and the central area 570 serves as the coating substrate. FIG. 9D shows a thermoformed film 400 held in place at the outer edge 560 by an adhesive attachment 580. FIG. 9E shows a film 400 that is formed as an integral part of the supporting foam 540. Such an integral film may be formed by any conventional means, for example, by welding or gluing a film directly to a foam piece or by treating the surface of a foam piece with heat or radiation to form a suitable film surface for use as a coating substrate.

A third aspect of the method of the present invention is shown in FIG. 10A. A microneedle array 850 is provided having a substrate 820 and microneedles 830 extending from the substrate. A coating solution 810 is placed in a coating reservoir block 802 having a coating substrate 804 and walls 806. In one embodiment, the coating substrate 804 may be a smooth metal surface. In another embodiment, the coating substrate 804 may be a thin, polymeric film or other flexible layer held against the top surface of the coating reservoir block 802. The coating solution 810 comprises a carrier fluid and a coating material. The coating solution 810 may be metered onto the coating substrate 804, such that the coating solution has a desired thickness. Alternatively, an excess of coating solution may be applied to the coating substrate and the coating solution is then subsequently adjusted to the desired thickness by removing fluid with a doctor blade. The flexible film 800 is flexibly mounted to a rod 870 and is part of a supporting assembly 860 and held in place with an attachment band 872. As shown, the flexible film 800 is supported by a pad 880 positioned between the rod 870 and the back of the flexible film 800. The back of the microneedle array 850 (i.e., the portion of the microneedle array opposed to the microneedles) is attached to the flexible film 800. The microneedle array 850 is thus flexibly mounted to the supporting assembly 860. The supporting assembly 860 and coating reservoir block 802 are brought towards each other such that the microneedle array 850 is brought into contact with the coating substrate 804 during a transfer step as shown in FIG. 10B, thereby bringing the coating solution 810 into contact with the microneedles 830. The supporting assembly 860 is then removed from the coating reservoir block 802 as shown in FIG. 10C, thereby transferring at least a portion of the coating solution 810 to the microneedle array 850. The transferred carrier fluid is then allowed to evaporate, thereby leaving a dried coating 830 on the microneedle array 850. The microneedle array 850 may be attached to the flexible film 800 by any conventional means, for example, by an adhesive bond or by a vacuum pulled through the flexible film 800 if the flexible film 800 is porous. In one embodiment, the microneedle array is temporarily attached to the flexible film 800, such as by a low-strength, repositionable adhesive. In another embodiment, the microneedle array may be permanently attached to the flexible film 800 in the form of a patch as described above. The patch backing will thus serve as the flexible film 800 and may be temporarily attached to the supporting assembly 860, such as by a vacuum.

Figure 11:
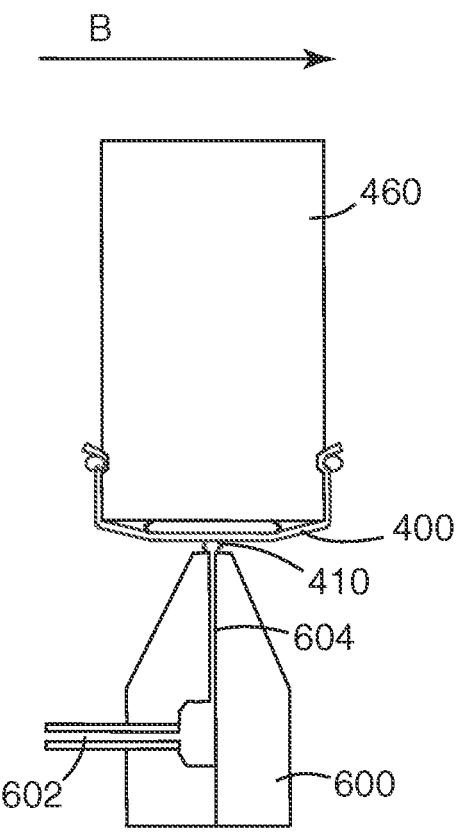
FIG. 11 is a schematic cross-sectional view of another embodiment of the present invention that employs an extrusion die.

When the coating solution is applied to a flexible film coating substrate, any of a number of conventional means may be used. The amount of coating solution applied is desirably metered so as to provide a controlled amount of coating solution on the coating substrate. For example, FIG. 11 shows use of an extrusion die 600 to directly apply coating solution 410 to a dauber assembly 460 having a flexible film 400 coating substrate. Coating solution is fed into the extrusion die 600 through an input line 602 and extruded out of a slot 604. The flexible film 400 coating substrate with coating solution 410 is subsequently moved (e.g., along the direction of the arrow labeled B) and brought into contact with a microneedle array as described above after the coating solution is applied.

Figure 12A:
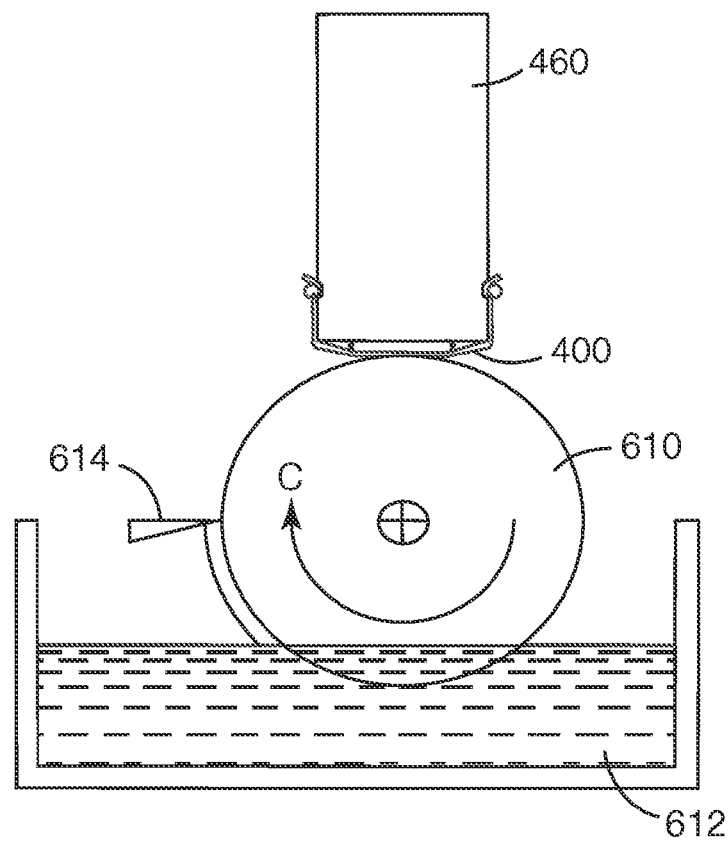
FIGS. 12A and B are schematic cross-sectional views of other embodiments of the present invention that employ a pickup roll.
Figure 12B:
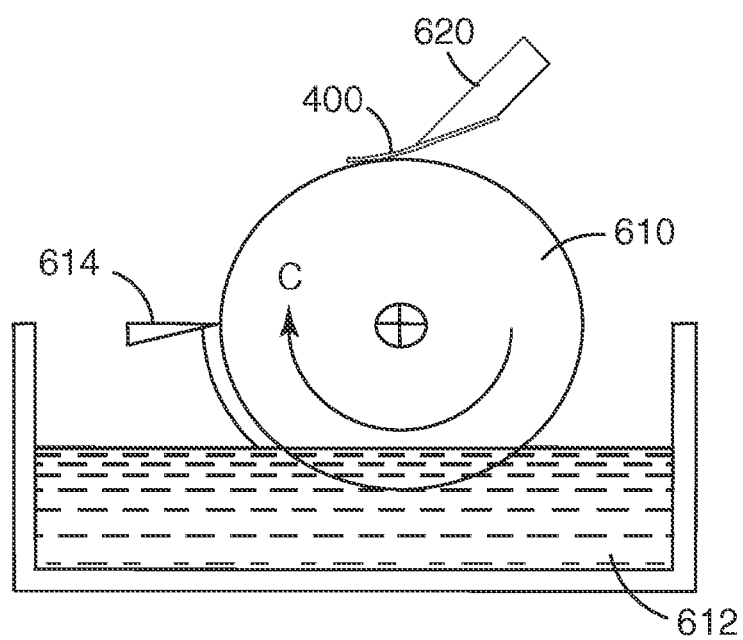

In one embodiment, a pickup roller feed system with a cylindrical surface onto which coating formulation is applied by any of several means may be used to transfer coating solution to a flexible film coating substrate. This is typically done by passing the flexible film over a pickup roller while the film is in slight contact with the surface of the roller or the surface of the layer of coating formulation. The surface of the pickup roller may rotate in the same direction as the motion of the passing film, or in opposing direction, at matching surface speeds or at an optimal speed ratio for the desired application volume. FIG. 12A shows use of a pickup roller 610 supplied by direct contact with the surface of the coating formulation in a supply reservoir 612. A doctor blade 614 may be used to wipe off excess material or meter the amount of material remaining on the surface of the roller. The doctor blade may be rigid or flexible (i.e. metallic or rubber), and may be in contact with or gapped slightly away from the surface of the pickup roller. Alternatively (not shown), an extrusion die or one or more micro tubes may be used to apply coating formulation directly to the surface of the pickup roller. The pickup roller 610 with applied coating solution is allowed to rotate and come into contact with the flexible film 400 coating substrate that is supported by a dauber assembly 460. FIG. 12B shows a similar example where the coating substrate is a flexible film 400 held by an angled film holder 620. In both figures, the arrow labeled C shows the direction of rotation of the pickup roller 610. As in previous figures, the dauber assembly 460 or flexible film 400 may be moved into contact with a microneedle array using any suitable means of motion.

Figure 13:
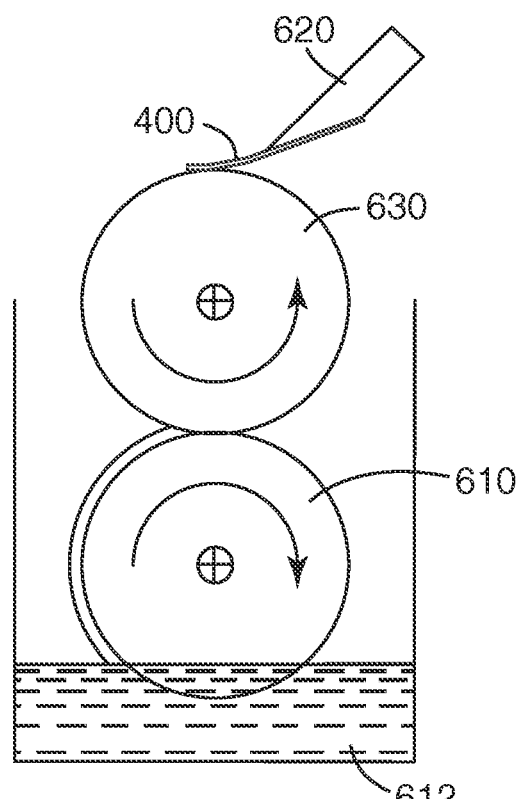
FIG. 13 is a schematic cross-sectional view of another embodiment of the present invention that employs a partner roll.

FIG. 13 shows use of a partner roll 630 to contact the surface of the coating formulation in the supply reservoir 612 while rotating in the opposite direction of the pickup roll 610 (direction of rotation of each roll shown by large arrow), while the gap between the two rolls controls the amount of material remaining on the surface of the partner roll prior to it coming in contact with the flexible film. The pickup roller 610 and partner roll 630 may be independently constructed of solid or conformable material (i.e. metal or rubber), and its surface may be smooth or it may be textured, for example, as a gravure roll or an anilox roll of a flexographic printer. Typically the partner roll 630 contacting the coating formulation in the supply reservoir 612 is made of a soft material which carries the coating formulation upward and into contact with the pickup roller 610 which removes excess coating formulation and subsequently transfers the metered coating formulation to the flexible film 400 coating substrate.

Figure 14A:
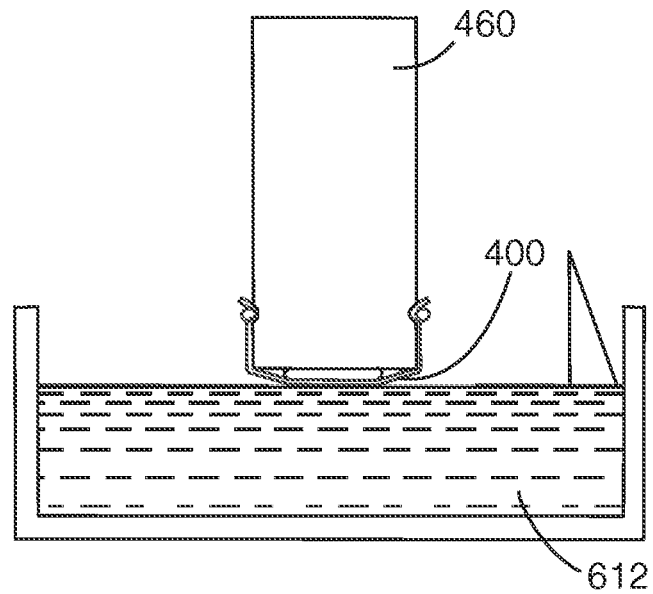
FIGS. 14A and 14B are schematic cross-sectional views of a portion of a coating apparatus in another embodiment of the present invention.
Figure 14B:
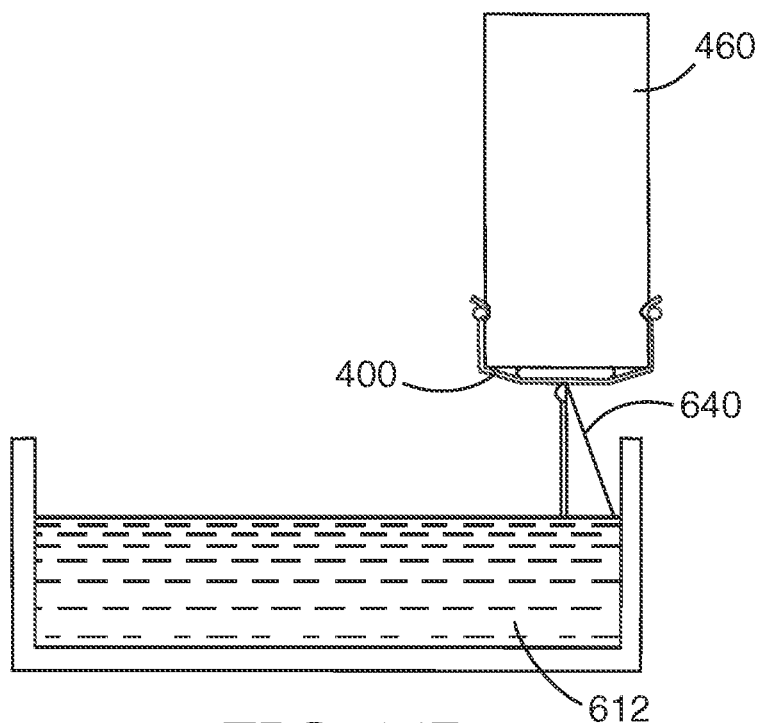

FIG. 14A shows a method of directly contacting the flexible film 400 coating substrate of the dauber assembly 460 with the surface of a coating formulation in a supply reservoir 612. The dauber may then be removed from the reservoir and passed over a doctoring blade 640, as shown in FIG. 14B, in order to wipe off excess coating formulation and thereby leave a desired thickness of coating formulation on the coating substrate of the dauber assembly 460.

Figure 15A:
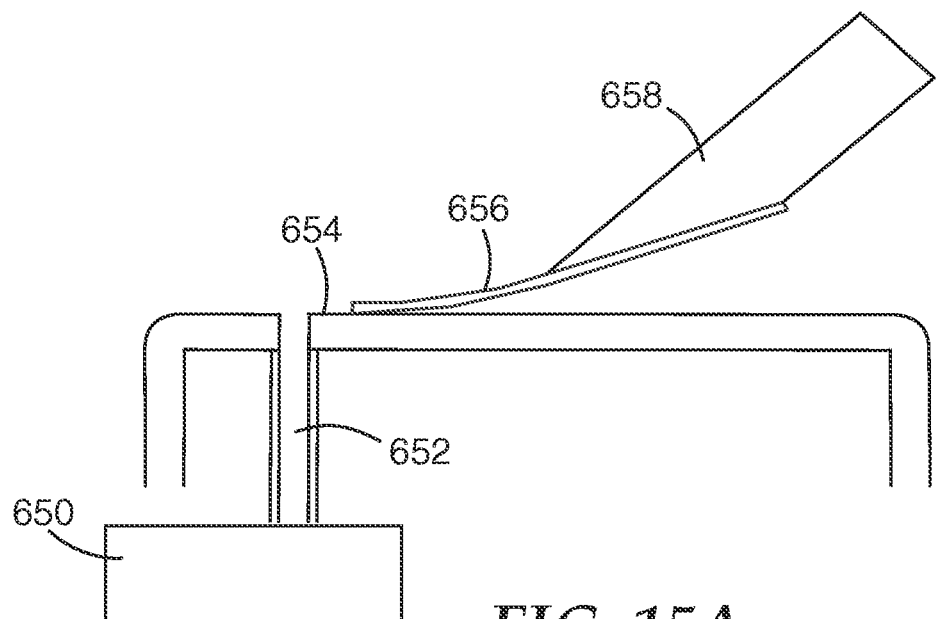
FIG. 15A is a schematic cross-sectional view of another embodiment of the present invention that employs a pickup plate.
Figure 15B:
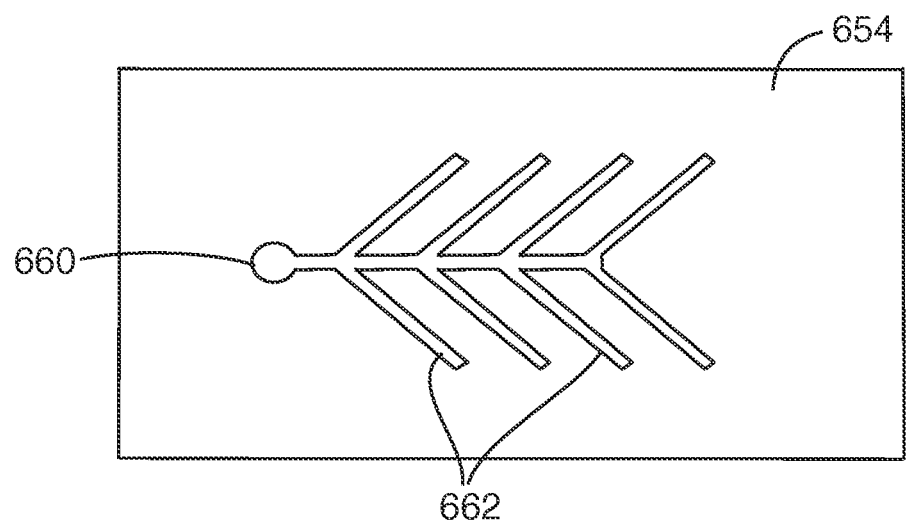
FIG. 15B is a schematic plan view of the embodiment in FIG. 15A where the pickup plate has a herringbone capillary pattern.
Figure 16A:
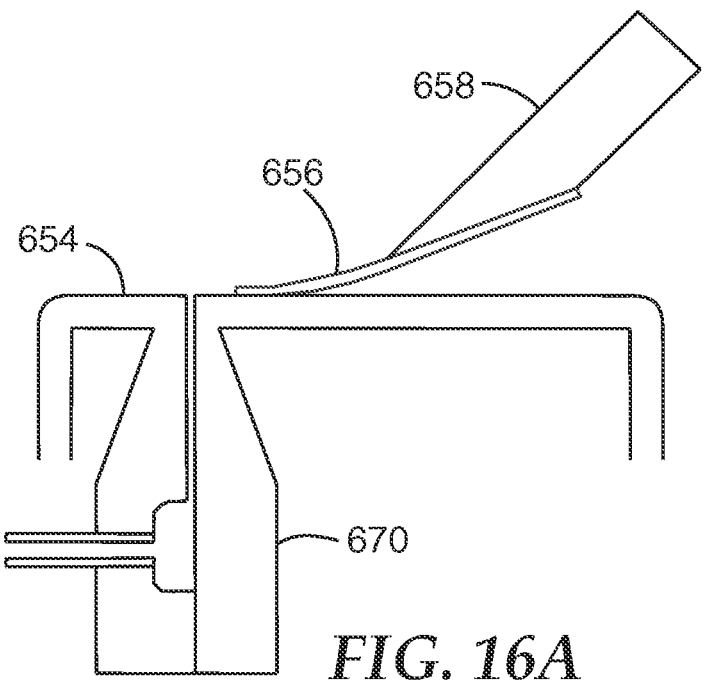
FIG. 16A is a schematic cross-sectional view of another embodiment of the present invention that employs a pickup plate and an extrusion die.
Figure 16B:
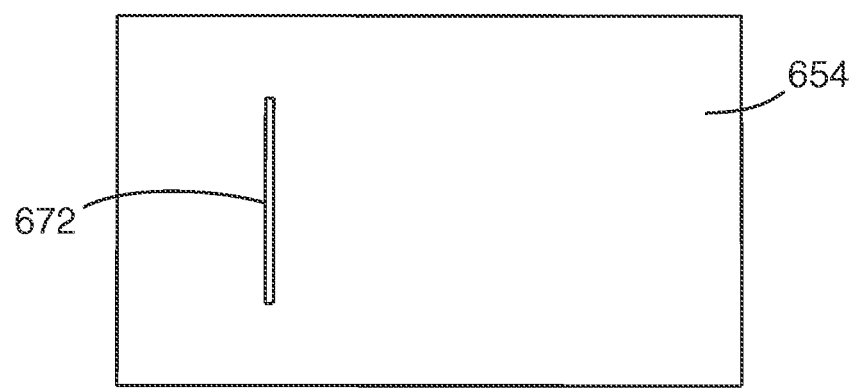
FIG. 16B is a schematic plan view of the embodiment in FIG. 16A.
Figure 17A:
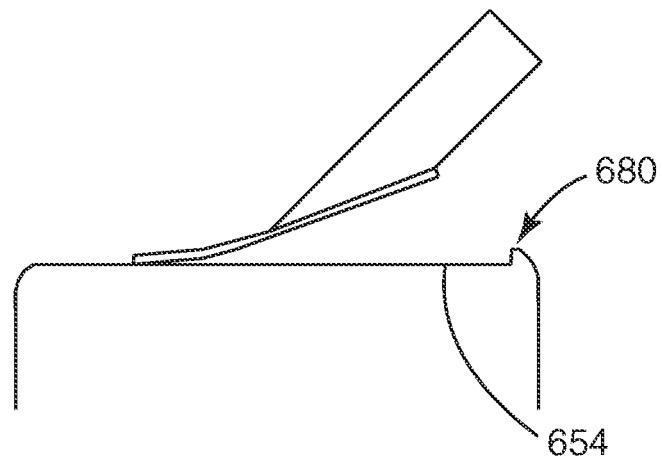
FIGS. 17A and 17B are schematic cross-sectional views of various doctoring features.
Figure 17B:
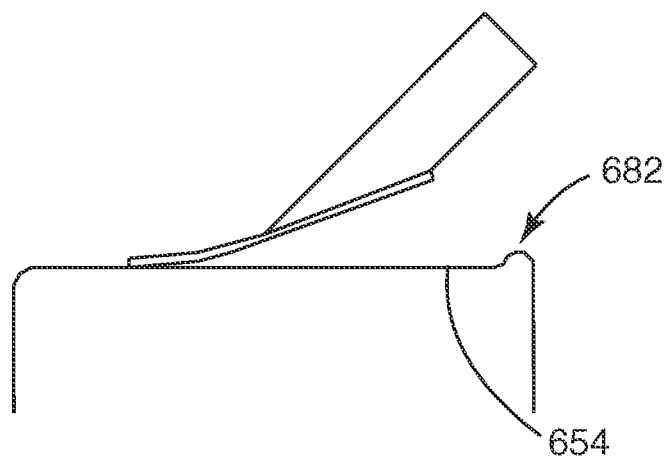

A pickup plate feed system is simply a surface onto which is applied coating formulation for subsequent transfer to a flexible film coating substrate, typically by passing the flexible film over the pickup plate while the flexible film is in slight contact with the surface of the plate. Typically flat and horizontal, the pickup plate may be supplied with coating formulation from above or below by any conventional means, such as with use of a pump and tubing or an extrusion die. FIG. 15A is a side view of a pump 650 and tube 652 that feed coating solution to the top surface of a pickup plate 654. A flexible film 656 held by an angled film holder 658 is shown passing over the pickup plate 654. FIG. 15B is a top view of the pickup plate 654 showing the tube opening 660 and capillary grooves 662 machined into the pickup plate in a herringbone pattern to serve as a means of spreading the coating formulation across the surface of the pickup plate 654. Any other suitable means of spreading the coating formulation on the surface of the pickup plate to a desired shape and size may be optionally employed, such as through use of an absorbent material, such as cheesecloth, applied to one end of the pickup plate. The absorbent material may lie on the surface of the pickup plate and wick the coating formulation uniformly outward from a supply orifice to a desired width for transfer. Absorbent material may be used alone or in conjunction with capillary grooves in the surface of the plate. Feeding and spreading of the coating formulation on the pickup plate can also be accomplished by integrating an extrusion die 670 into the bottom surface of the pickup plate 654 as shown in FIGS. 16A, B. The outlet 672 of the extrusion die is sized and spaced appropriately to feed a desired amount of coating formulation to the pickup plate for transfer to a flexible film. An optional doctoring feature for wiping excess coating formulation from the applicator may be used in conjunction with a pickup plate. FIG. 17A shows a sharp doctoring feature 680 integrated directly into the pickup plate 654. FIG. 17B shows a rounded doctoring feature 682 integrated directly into the pickup plate 654. Other suitable shapes, such as a bluntly serrated shape, may be used for the doctoring feature. Although the feeding mechanisms shown in FIGS. 15 to 17 are illustrated as transferring coating solution to a flexible film held by an angled film holder, it should be understood that these mechanisms are equally suitable for transfer of coating solution to any type of flexible film, such as a flexible film supported by a dauber assembly as described above. The trailing edge will generally be aligned so that it moves in a plane parallel to the plane of the bottom surface of the pickup plate and will be aligned in height so that it will interfere with the fluid on the pickup plate. In one embodiment, the trailing edge may be aligned so that it moves in a plane that is below the bottom surface of the pickup plate, so that the trailing edge interferes with both the pickup plate and the coating fluid. This distance between the plane of motion of the trailing edge and the top surface of the pickup plate is referred to as the edge-plate interference and is typically between about 0 and about 2 mm, sometimes between about 0 and about 1 mm.

In all of the foregoing embodiments the coating fluid may form a relatively thin film on the coating substrate just prior to a transfer step. The thickness of coating fluid on the coating substrate prior to a transfer step is typically less than or equal to the height of at least one of the microneedles and often less than or equal to the height of all of the microneedles. The thickness of coating fluid on the coating substrate prior to a transfer step may be between about 25% and 75% of the height of the microneedles and sometimes between about 30% and 50% of the height of the microneedles. Adjustment of the coating fluid thickness to such dimensions may be particularly beneficial in allowing preferential deposition of coating solution and coating material onto the tips of the microneedles.

The viscosity of the coating fluid will depend on a number of parameters, including the types and amounts of carrier fluid(s), dissolved or dispersed coating materials, and additional excipients, as well as the temperature of the coating fluid. In one embodiment, it may be desirable to cool the coating fluid to a temperature below room or ambient temperature, but above the freezing point of the coating fluid. Such cooling may improve the ability to deposit a dried coating material by, for example, increasing the viscosity of the coating fluid or reducing any tendency of the coating fluid to evaporate prior to transfer to the microneedle array. The temperature of the coating fluid may be controlled by any of a number of conventional methods. For example, the environmental temperature surrounding the entire apparatus may be controlled such that the coating fluid, coating substrate, and microneedle array are all held at a fixed, uniform temperature. Alternatively, various items may be selectively cooled, such as the coating substrate, the microneedle array, a pickup roller or pickup plate, if employed, and/or the coating fluid reservoir. In one embodiment the viscosity of the coating solution may be greater than or equal to the viscosity of water at ambient temperature (i.e., about 1 centipoise or cP). Viscosity may be measured by any conventional means, such as with a cone and plate, controlled shear rate rheometer at a given shear rate. In one embodiment, the viscosity at a shear rate of 50 sec$^{-1}$ is greater than 4 cP, often greater than 10 cP, and sometimes greater than 20 cP. In one embodiment, the viscosity at a shear rate of 50 sec$^{-1}$ is less than 1500 cP, often less than 500 cP, and sometimes less than 100 cP.

The microneedle devices useful in the various embodiments of the invention may comprise any of a variety of configurations, such as those described in the following patents and patent applications, the disclosures of which are herein incorporated by reference. One embodiment for the microneedle devices comprises the structures disclosed in U.S. Pat. No. 6,881,203. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle devices comprises the structures disclosed in co-pending U.S. Patent Application Publication No. 2005/0261631, which describes microneedles having a truncated tapered shape and a controlled aspect ratio. Still another embodiment for the microneedle devices comprises the structures disclosed in U.S. Pat. No. 6,091,975 (Daddona, et al.) which describes blade-like microprotrusions for piercing the skin. Still another embodiment for the microneedle devices comprises the structures disclosed in U.S. Pat. No. 6,313,612 (Sherman, et al.) which describes tapered structures having a hollow central channel. Still another embodiment for the micro arrays comprises the structures disclosed in International Publication No. WO 00/74766 (Gartstein, et al.) which describes hollow microneedles having at least one longitudinal blade at the top surface of tip of the microneedle.

The surface of the microneedles may be altered with a surface pre-treatment, such as a plasma treatment capable of altering surface functionality. For example, polycarbonate may be plasma treated with a nitrogen plasma to cause amide functionalization or with an oxygen plasma to cause carboxylate functionalization. A combination of nitrogen and oxygen plasma treatment may be used to give a mixed surface functionality. Alternatively, the surface of the microneedles may be treated with a coating to alter the surface properties. Such a coating may be directly applied as a solid material, such as through use of heat or plasma deposition. Examples of thin layers of material cured onto the array include plasma deposited diamond-like glass films, such as those described in U.S. Pat. No. 6,881,538 (Haddad, et al.), ultraviolet polymerized acrylates, such as those described in U.S. Pat. No. 5,440,446 (Shaw, et al.), plasma deposited fluoropolymers, or any other thin layer that may be applied by conventional coating method, such as spray coating or roll coating and subsequently crosslinked using any suitable radiation. In one embodiment, a diamond-like glass film may be deposited on the microneedles and subsequently treated with an oxygen plasma to make the surface hydrophilic.

Microneedle devices suitable for use in the present invention may be used to deliver therapeutic agents or drugs (including any pharmacological agent or agents) through the skin in a variation on transdermal delivery, or to the skin for intradermal or topical treatment, such as vaccination.

In one aspect, drugs that are of a large molecular weight may be delivered transdermally. Increasing molecular weight of a drug typically causes a decrease in unassisted transdermal delivery. Microneedle devices suitable for use in the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle devices suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamidronate; and molecules with physicochemical properties that are not conducive to passive transdermal delivery.

In another aspect, microneedle devices suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamidronate; and molecules with physicochemical properties that are not conducive to passive transdermal delivery.

In another aspect, microneedle devices suitable for use in the present invention may have utility for enhancing delivery of molecules to the skin, such as in dermatological treatments, vaccine delivery, or in enhancing immune response of vaccine adjuvants. Examples of suitable vaccines include flu vaccine, Lyme disease vaccine, rabies vaccine, measles vaccine, mumps vaccine, chicken pox vaccine, small pox vaccine, hepatitis vaccine, pertussis vaccine, rubella vaccine, diphtheria vaccine, encephalitis vaccine, yellow fever vaccine, recombinant protein vaccine, DNA vaccine, polio vaccine, therapeutic cancer vaccine, herpes vaccine, pneumococcal vaccine, meningitis vaccine, whooping cough vaccine, tetanus vaccine, typhoid fever vaccine, cholera vaccine, tuberculosis vaccine, and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Patent Application Publication No. 2004/0049150, the disclosure of which is hereby incorporated by reference.

Microneedle devices may be used for immediate delivery, that is where they are applied and immediately removed from the application site, or they may be left in place for an extended time, which may range from a few minutes to as long as 1 week. In one aspect, an extended time of delivery may be from 1 to 30 minutes to allow for more complete delivery of a drug than can be obtained upon application and immediate removal. In another aspect, an extended time of delivery may be from 4 hours to 1 week to provide for a sustained release of drug.

EXAMPLES

Tetanus Toxoid Total-Array Content by High Performance Liquid Chromatography (HPLC)

A sample extraction solvent was prepared containing 50 mM potassium perchlorate, 50 mM potassium citrate, 20 mM sodium phosphate, 376 mM sodium chloride, and 100 µg/mL bovine serum albumin. An HPLC sample solution was prepared by placing an array into a polypropylene cup, adding 1.0 mL of the sample extraction solvent to the cup, snapping a cap onto the sample cup, and sonicating for 30 minutes.

Gradient elution HPLC (Mobile phase A): 0.2% (v/v) perchloric acid; Mobile phase B: 10% water, 88% acetonitrile, 2% isopropanol, 0.2% perchloric acid (70%); Solvent Program: 0.00 min, 22% B, 1.0 mL/min; 6.00 min, 58% B, 1.0 mL/min; 6.01 min, 100% B, 1.0 mL/min; 6.50 min, 100% B, 0.5 mL/min; 10.0 min, 0% B, 0.5 mL/min; Injection Volume: 100 µL; Column: Zorbax 300SB-C8 50×4.6 mm, 3.5 micron) was used to quantify tetanus toxoid in the HPLC sample solution.

Non-adjuvanted tetanus toxoid (TT) vaccine (Aventis) was calibrated against a lyophilized TT primary standard (List Biologics) and used as a working standard. The working standard was used to obtain a calibration curve from approximately 1 µg-TT/mL to 28 µg-TT/mL. The correlation coefficient for the linear regression of the calibration curve was typically greater than 0.999. Tetanus toxoid content results are the average of between 6 and 10 replicates.

Tetanus Toxoid Tip-Content by High Performance Liquid Chromatography (HPLC)

Tetanus toxoid content on the tips of the microneedles was measured by fixing the toxoid in place on the substrate and lower portions of the microneedles so that it could not be extracted into the HPLC sample solution. A microneedle array was placed on a flat surface with the needles pointing upward and 10 μL of an oil-based polyurethane coating solution (Minwax® Fast-Drying Polyurethane) was applied to the array and allowed to coat the substrate of the array. The polyurethane was allowed to cure for at least 3 hours at ambient conditions. The array was subsequently extracted and analyzed as described in the total content method.

Aluminum Content by Inductively Coupled Plasma (ICP)

A 0.5 mL aliquot of the HPLC sample solution (described above) was diluted to 5.0 mL with 4% nitric acid for analysis of aluminum by ICP. The analysis was calibrated by using aluminum standards at 1, 2, 4, 5, 6, 8 and 11 μg/mL. The correlation coefficient for the linear regression of the calibration curve was typically greater than 0.999.

Enzyme-Linked Immunosorbent Assay (ELISA)

Quantitative determination of anti-tetanus toxoid IgG from rabbit serum was performed by ELISA. Tetanus toxoid is coated on the solid phase and binds anti-tetanus toxoid IgG from rabbit serum samples. Plates are washed and bound rabbit IgG is detected with an anti-rabbit IgG-HRP conjugate. The assay was standardized against the EP veterinary standard rabbit anti-tetanus toxoid BRP Batch 1 (EDQM-European Pharmacopeia Commission catalog number C2425600). 1000 arbitrary units (AU) from this ELISA is equivalent to 1 international unit (IU). Unless otherwise noted, anti-tetanus toxoid IgG results are reported as the geometric average of 5 replicates.

Microneedle Arrays

Microneedle arrays were prepared as follows. A circular disk (area 2 $cm^2$, thickness 1.02 mm) that was partially patterned with an array of microneedles (37×37) in a square shape (1 $cm^2$) centered on one side of the disk was prepared. The needles were regularly spaced with a distance of 275 microns between the tips of adjacent needles in a square-shaped pattern. Individual needles were pyramidal in shape with a height of 250 microns and a square base having a side-length of 83.3 microns. The tips were truncated with a flat, square-shaped top having a side-length of 5 microns. Arrays were injection molded according to the general description provided in International Patent Application Publication No. WO 05/82596 and made from polycarbonate (Lexan® HPS1R-1125, GE Plastics, Pittsfield, Mass.). The center of the disk was then die cut to provide a microneedle array (area=1 $cm^2$) having microneedles on approximately 90% of the surface of the patterned side of the disk. The microneedle array had approximately 1200 microneedles.

Example 1

A stock coating formulation was prepared as follows. An aluminum hydroxide adjuvant (Alhydrogel 85™, Brenntag Biosector Co. Denmark) was used for adsorption of tetanus toxoid according to the procedure provided by the manufacturer. An amount (5 mL) of tetanus toxoid (TT) (Statens Serum Institute Lot 92-1, 888 Lf/mL) was added dropwise to aluminum hydroxide adjuvant (5 mL) solution while vortexing for 2 minutes. The adsorption process was continued by mixing the formulation for another 20 minutes at room temperature using a horizontal shaker. The mixture was then desalted and concentrated by centrifugation. After final centrifugation at 2000 rpm for 10 min, the precipitate of adsorbed TT was resuspended in sucrose solution to provide a 14% (w/v) sucrose solution of adjuvanted tetanus toxoid. All formulations were stored at 4° C.

Microneedle arrays were prepared as described above and treated as follows. The arrays were plasma treated using a Plasma-Therm VII 7000 series plasma processing system. A diamond-like glass thin film was formed through plasma deposition by feeding a mixture of tetramethyl silane (150 standard cubic centimeter per minute, sccm) and oxygen (200 sccm) gas in an unpressurized plasma with 2000 W RF power applied for 15 seconds. The arrays were then subsequently treated with an oxygen plasma (400 sccm) under a pressure of 150 mTorr with 300 W power for 60 seconds to remove elemental and covalently bonded carbon from the surface atomic layers and to make the surface hydrophilic.

An apparatus as generally shown in FIG. 3A, B with a flexible film as shown in FIG. 1 was used to apply the coating formulation to the microneedle arrays. The flexible film was a nylon filter membrane (127 μm thick) with 0.45 micron pore size (Alltech Associate, Inc.) that was mounted to a rotational arm aligned so as to rotate in a plane parallel to the surface of the microneedle array to be coated. The portion of the flexible film extending from the rotational arm was approximately 1.5 cm wide by 0.75 cm long. A supporting piece of polyester (76 μm thick, 44125 green color coded plastic shim, Precision Brand Products) was mounted behind the nylon filter membrane. The supporting polyester piece was approximately 1.5 cm wide by 0.55 cm long and aligned so that the trailing edge of the flexible film extended about 0.2 cm beyond the trailing edge of the polyester film piece. The arm was aligned so that the trailing edge of the flexible film was approximately 0.035 inch (889 μm) below the plane formed by the tips of the microneedles on the array. The flexure angle of the film was approximately 15 degrees.

A pickup plate, as generally shown in FIG. 17B was used to apply solution to the flexible film. The arm was aligned so that the trailing edge of the flexible film was moved in a plane parallel to and a distance below the plane of the top surface of the pickup plate. This distance, referred to as the edge-plate interference, was 0.030 inch (762 μm). The trailing edge thus interfered with the top surface of the pickup plate. Coating formulation was applied to the top surface of the pickup plate and transferred to the flexible film. Before each transfer step, approximately 5 μL of the coating formulation was applied to the pickup plate. The flexible film was advanced over the surface of the array at a speed of approximately 9 cm/sec so that the trailing edge of the film contacted the needle tips and was brushed over the surface of the array. The array was rotated 90 degrees in between each individual transfer step. The transfer step was repeated 5-8 times until dried formulation in a teardrop shape with an approximate maximum dimension of 70 microns was formed at a height on the microneedles of approximately 100 to 125 microns above the substrate of the microneedle array. The coated arrays were allowed to dry at room temperature and humidity.

Tetanus toxoid total-array content as measured by reversed phase HPLC was 9.5 μg (st. dev.=4.6 μg). Aluminum content of the coated array as measured by ICP was 12 μg (st. dev.=5 μg).

Example 2

Coated microneedle arrays were prepared as in Example 1 with the exception that the amount of tetanus toxoid was reduced by half. Tetanus toxoid total-array content as measured by reversed phase HPLC was 5.7 μg (st. dev.=1.2 μg). Aluminum content of the coated array as measured by ICP was 8 μg (st. dev.=4 μg).

In Vivo Anti-Tetanus Toxoid IgG and Tetanus Toxoid Removal

Microneedle devices were prepared by adhering antigen coated arrays as described in Examples 1 to 3 to an adhesive backing. The arrays were applied to New Zealand White female rabbits (N=5) using an applicator as generally described in PCT Publication No. WO 2005/123173, the disclosure of which is hereby incorporated by reference. The applicator piston mass was 2.88 g and the devices were applied at a velocity of 6.19 meters/second. An area on the abdomen of each rabbit was closely clipped and shaved, taking care not to irritate the skin. One device was applied to each rabbit and allowed to remain in place for 20 minutes before removal. A second device (with the same coating as the first device) was applied to each rabbit 14 days after the initial application and again allowed to remain in place for 20 minutes before removal. A serum sample was taken from each rabbit 21 days after the initial application and analyzed for the level of anti-tetanus toxoid IgG by ELISA. The anti-tetanus toxoid IgG results are reported as the geometric mean of the 5 replicates. The results are summarized in Table 1. The residual amount of tetanus toxoid in the arrays removed from the rabbits was tested by HPLC. The amount of tetanus toxoid removed from the array was determined by taking the difference between the initial tetanus toxoid level and the residual tetanus toxoid level. The results are summarized in Table 1.

In addition, testing (indicated below as 2×) was performed where two arrays were applied to each rabbit at each application time, thus providing a double dose. Amount of tetanus toxoid removed is reported as the total removed from both arrays.

TABLE 1

| Array Example No. | anti-tetanus toxoid IgG [AU] | tetanus toxoid removed [μg] |
|---|---|---|
| 1 | 4573 | 2.6 |
| 1 (2X) | 6532 | 6.2 |
| 2 | 1187 | 3.1 |
| 2 (2X) | 5547 | 5.8 |

Example 3

An antigen coating formulation was prepared as follows. Tetanus toxoid (Statens Serum Institute Lot 92-1, 888 Lf/mL) was concentrated by centrifugation with a 30,000 g/mol MW cut-off membrane to provide a concentrated tetanus toxoid stock solution (3554 Lf/mL). A 70% (w/v) sucrose stock solution was prepared. An aliquot (1.124 mL) of tetanus toxoid stock solution, an aliquot (5.179 mL) sucrose stock solution, and water (0.930 mL) were added together and mixed to form the antigen coating formulation. The nominal sucrose concentration was 50% (w/v).

An apparatus as generally shown in FIG. 3A, B with a flexible film as shown in FIG. 1 was used to apply the coating formulation to the microneedle arrays. A diamond-like glass film was deposited and treated as described in Example 1. The flexible film was a nylon filter membrane (127 μm thick) with 0.45 micron pore size (Alltech Associate, Inc., Deerfield, Ill.) that was mounted to a rotational arm aligned so as to rotate in a plane parallel to the surface of the microneedle array to be coated. The portion of the flexible film extending from the rotational arm was approximately 1.5 cm wide by 0.75 cm long. A supporting piece of polyester (76 μm thick, 44125 green color coded plastic shim, Precision Brand Products) was mounted behind the nylon filter membrane. The supporting polyester piece was approximately 1.5 cm wide by 0.55 cm long and aligned so that the trailing edge of the flexible film extended 0.20 cm beyond the trailing edge of the polyester film piece. The arm was aligned so that the trailing edge of the flexible film moved in a plane parallel to approximately 0.015 inch (381 μm) below the plane formed by the tips of the microneedles on the array. This distance is referred to as the edge-array interference. The flexure angle of the film was approximately 7 degrees.

A pickup plate, as generally shown in FIG. 17B was used to apply solution to the flexible film. The arm was aligned so that the trailing edge of the flexible film moved in a plane 0.030 inch (762 μm) below the plane of the top surface of the pickup plate (i.e., the edge-plate interference was 762 μm). Coating formulation (7 μL) was applied to the top surface of the pickup plate. The flexible film was advanced over the surface of the pickup plate at a speed of approximately 9 cm/sec so that the trailing edge of the film contacted the coating formulation in order to transfer coating formulation to the flexible film. The flexible film was then advanced over the surface of the array at a speed of approximately 9 cm/sec so that the trailing edge of the film contacted the needle tips and was brushed over the surface of the array. The step of transferring fluid from the pickup plate to the film and subsequently to the array was repeated 4 to 6 times until the coating formulation was used up. The array was rotated 90 degrees in between each individual transfer step. Tetanus toxoid total-array content as measured by reversed phase HPLC was 12.9 μg (st. dev.=5.2 μg).

Examples 4-9

An antigen coating formulation was applied to microneedle arrays according to the procedure described in Example 3 with the exception that one or more of the following parameters was varied: flexure angle, edge-array interference, edge-plate interference, stroke rate. The parameter values and the resultant tetanus toxoid total-array contents as measured by reversed phase HPLC are shown in Table 2.

TABLE 2

| Example No. | flexure angle [degrees] | edge-array interference, inch [μm] | edge-plate interference, inch [μm] | film velocity [cm/sec] | tetanus toxoid content [μg] |
|---|---|---|---|---|---|
| 4 | 7  | 0.005 [127] | 0.030 [762] | 9  | 8.7 (2.4) |
| 5 | 7  | 0.015 [381] | 0.030 [762] | 15 | 21.3 (12.5) |
| 6 | 15 | 0.035 [889] | 0.000       | 15 | 10.0 (5.6) |
| 7 | 15 | 0.005 [127] | 0.000       | 9  | 7.6 (4.6) |
| 8 | 15 | 0.035 [889] | 0.030 [762] | 9  | 6.5 (1.1) |
| 9 | 15 | 0.005 [127] | 0.030 [762] | 9  | 8.0 (1.7) |

Example 10

A coating solution was prepared as follows. Approximately equal amounts of sucrose and water were mixed along with a small amount of green food coloring (approximately 0.25% by volume) to aid in visualization. The solution was heated to 235° F. (112.8° C.) to form a sucrose solution having about 75 to 80% solids, cooled for at least 12 hours and decanted to separate the sucrose solution from the undissolved or recrystallized solids.

A coating apparatus as generally described in FIG. 12A was used to apply the coating solution to a microneedle array. The dauber assembly was prepared by adhering a 0.625 inch (1.59 cm) diameter×0.020 inch (0.051 cm) thick disk of double-sided, medium density polyethylene foam tape (3M Cushion-Mount™ Plus no. 1020) to one end of a 0.65 inch (1.65 cm) diameter×2.0 inch (5.08 cm) long polyurethane foam rod (Aquazone®, density=1.8 lb/cu. Ft, 25% compression deflection of 0.56 psi (3.86 kPa) as tested by ASTM D 3574, Foamex International Inc., Linwood, Pa.). A 0.20 inch (0.51 cm) thick×0.625 (1.59 cm) inch diameter brass disk was adhered to the exposed side of the double-sided foam tape. Another disk of foam tape was adhered to the brass disk and a 0.005 inch (127 μm) thick×0.625 (1.59 cm) inch diameter piece of Nylon filtration membrane (0.45 μm pore size, Alltech Associate, Inc., Deerfield, Ill.) was adhered to the exposed side of the second piece of double-sided foam tape. The laminate construction was thus: foam rod/foam tape/brass disk/foam tape/nylon membrane. A 1.020 inch (2.59 cm) diameter grooved roll with a face width of 1 inch (2.54 cm) was used as the pickup roll. The pickup roll had a groove spacing of 0.012 inch (305 μm), groove angle of 90 degrees, a nominal groove depth of 0.0060 inch (152 μm), and a nominal groove volume of 0.00360 cubic inch per square inch (0.00914 mL per cm²) of roll surface. The pickup roll was centered in a reservoir trough holding the coating solution described above. The reservoir trough was cylindrical in shape with a diameter of 1.062 inch (2.70 cm). The doctor blade was a 0.0625 inch (0.159 cm) thick polyurethane sheet with a Shore A hardness of 95 and was held in place by a 0.0625 inch (0.159 cm)×0.5 inch (1.27 cm) strip of stainless steel.

Coating solution was applied to the nylon membrane of the dauber assembly as generally shown in FIG. 12A. The pickup roll was rotated so as to fill the grooves with coating solution. The doctor blade was placed into contact with the pickup roller. The nylon membrane was then passed over the surface of the grooved roll several times until the amount of coating formulation on the nylon membrane reached equilibrium. The dauber assembly with coating fluid was then translated to a coating station where it was positioned directly above a microneedle array. It was then moved vertically to bring it into contact with the array as depicted in FIGS. 8A-C, subsequently cycled up and down a specified number of times in order to deposit coating formulation on the array, and then allowed to dry at ambient conditions. The microneedle array exhibited a light green color indicating that the sucrose solution was coated on the array after 12 deposition cycles. Microscopic examination showed that the coating was deposited in a generally spherical shape at or near each microneedle tip with an approximate diameter of 30 to 50 μm.

Example 11

A microneedle array was coated as described in Example 10 with the following exceptions. The pickup roll had a groove spacing of 0.012 inch (305 μm), groove angle of 60 degrees, a nominal groove depth of 0.0104 inch (264 μm), and a nominal groove volume of 0.00624 cubic inch per square inch (0.01584 mL per cm²) of roll surface. The microneedle array exhibited a strong, non-uniform green color after 4 deposition cycles. Microscopic examination showed that the coating was deposited in a generally spherical shape at or near each microneedle tip with an approximate diameter of 30 to 80 μm.

Example 12

A microneedle array was coated as described in Example 11 with the exception that 10 deposition cycles were used. The microneedle array exhibited a strong, uniform green color. Microscopic examination showed that the coating was deposited in a generally spherical shape at or near each microneedle tip with an approximate diameter of 60 to 100 μm.

Example 13

A microneedle array was coated as described in Example 11 with the exception that the doctor blade was spaced about 1 mil (25 μm) away from the pickup roller and a single deposition cycle was used. The microneedle array exhibited a light, uniform green color. Microscopic examination showed that the coating was deposited in a generally teardrop shape at or near each microneedle tip with an approximate diameter (measured in a plane parallel to the array substrate at the widest part of the teardrop) of 30 to 50 μm.

Example 14

A microneedle array was coated as described in Example 10 with the following exceptions. The pickup roll had a groove spacing of 0.014 inch (356 μm), groove angle of 90 degrees, a nominal groove depth of 0.0070 inch (178 μm), and a nominal groove volume of 0.00490 cubic inch per square inch (0.02156 mL per cm²) of roll surface. The microneedle array exhibited a light, non-uniform, green color after 8 deposition cycles. Microscopic examination showed that the coating was deposited in a generally spherical shape at or near each microneedle tip with an approximate diameter of 30 to 60 μm.

Example 15

A microneedle array was coated as described in Example 14 with the exception that the doctor blade was spaced about 2 mil (50 μm) away from the pickup roller and a single deposition cycle was used. The microneedle array exhibited a light, uniform green color. Microscopic examination showed that the coating was deposited in a generally teardrop shape at or near each microneedle tip with an approximate diameter (measured in a plane parallel to the array substrate at the widest part of the teardrop) of 40 to 50 μm.

Example 16

A microneedle array is coated as follows. A coating apparatus as generally described in FIG. 10A is used to apply a coating solution to a microneedle array. The supporting assembly is prepared by adhering a 0.625 inch (1.59 cm) diameter×0.020 inch (0.051 cm) thick disk of double-sided, medium density polyethylene foam tape (3M Cushion-Mount™ Plus no. 1020) to one end of a 0.65 inch (1.65 cm) diameter×2.0 inch (5.08 cm) long polyurethane foam rod (Aquazone®, density=1.8 lb/cu. Ft, 25% compression deflection of 0.56 psi (3.86 kPa) as tested by ASTM D 3574, Foamex International Inc., Linwood, Pa.). The non-patterned side of a microneedle array is adhered to the exposed surface of the double-sided foam tape.

A stainless steel reservoir is used having a trough-shaped reservoir large enough to allow the microneedle array to be placed fully within the trough. Another disk of foam tape is adhered to the trough of the reservoir and a 0.005 inch (127 μm) thick×0.625 (1.59 cm) inch diameter piece of Nylon filtration membrane (0.45 μm pore size, Alltech Associate, Inc., Deerfield, Ill.) is adhered to the exposed side of the second piece of double-sided foam tape. An excess of coating solution is applied to the Nylon filtration membrane and adjusted to a thickness of about one-half the height of the microneedles by removing excess fluid with a doctor blade. The coating solution is an aqueous sucrose solution having from 40 to 70% (w/w) sucrose. A transfer step is performed by bringing the supporting assembly towards the reservoir so that the microneedles come into contact with both the Nylon filtration membrane and the coating solution. The supporting assembly is then removed from contact with the Nylon filtration membrane and the coating solution. The array is allowed to dry under ambient conditions. Repeated transfer steps may be employed to transfer additional coating material until the dried coating material forms a teardrop shape near the tip of each microneedle.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A method of coating a microneedle array comprising:
   providing a microneedle array having a substrate and a plurality of microneedles;
   applying a coating solution comprising a carrier fluid and a coating material onto a first major surface of a flexible film;
   performing a transfer step of bringing the first major surface of the flexible film into contact with the microneedles and removing the flexible film from contact with the microneedles, wherein at least a portion of the coating solution is transferred to the microneedle array during the transfer step, and wherein the flexible film is moved in a linear direction across the microneedles while the coating solution on the first major surface of the flexible film is in contact with the microneedles; and
   allowing the carrier fluid to evaporate to leave a dried coating on the microneedle array.

2. A method as claimed in claim 1, wherein the flexible film and the microneedle array define an angle of flexure during the transfer step that is between 0 and 90 degrees.

3. A method as claimed in claim 2 wherein the angle of flexure is between 5 and 15 degrees.

4. A method as claimed in claim 1 wherein the linear direction is selected from the group consisting of generally parallel to the plane of the microneedle array and generally perpendicular to the plane of the microneedle array.

5. A method as claimed in claim 1 wherein more than one transfer step is performed.

6. A method as claimed in claim 4 wherein more than one transfer step is performed and in between repeated transfer steps the microneedle array is rotated with respect to the flexible film in a plane generally parallel to the plane of the microneedle array substrate.

7. A method as claimed in claim 1 wherein the amount of coating solution transferred to the microneedles during a transfer step is between 0.1 μL and 10 μL.

8. A method as claimed in claim 1 wherein more than 50% by weight of the dried coating applied to the microneedle array is present on the needles.

9. A method as claimed in claim 1 wherein the dried coating material is preferentially deposited onto the microneedles.

10. A method as claimed in claim 1 wherein the dried coating material is preferentially deposited onto the upper half of the microneedles.

11. A method as claimed in claim 1 wherein the coating solution comprises a therapeutic agent.

12. A method as claimed in claim 11 wherein the therapeutic agent is present in the coating solution as a dispersed or suspended material.

13. A method as claimed in claim 1 wherein the coating solution comprises water.

14. A method as claimed in claim 1 wherein the coating solution comprises a vaccine, vaccine adjuvant, or mixture thereof.

15. A method as claimed in claim 1 wherein the surface of the microneedles is hydrophilic.

16. A method as claimed in claim 1 wherein the surface of the microneedles is coated with a thin film of diamond-like glass.

17. A method of coating a microneedle array comprising:
   providing a microneedle array having a substrate and a plurality of microneedles;
   applying a coating solution comprising a carrier fluid and a coating material onto a first major surface of a flexible film;
   performing a transfer step of bringing the first ma or surface of the flexible film into contact with the microneedles and removing the flexible film from contact with the microneedles, wherein at least a portion of the coating solution is transferred to the microneedle array during the transfer step, and wherein the flexible film and the microneedle array define an angle of flexure during the transfer step that is between 5 and 15 degrees; and
   allowing the carrier fluid to evaporate.

18. A method of coating a microneedle array comprising:
providing a microneedle array having a substrate and a plurality of microneedles, wherein the surface of the microneedles is coated with a thin film of diamond-like glass;
applying a coating solution comprising a carrier fluid and a coating material onto a first major surface of a flexible film;
performing a transfer step of bringing the first ma or surface of the flexible film into contact with the microneedles and removing the flexible film from contact with the microneedles, wherein at least a portion of the coating solution is transferred to the microneedle array during the transfer step; and
allowing the carrier fluid to evaporate.

19. A method of coating a microneedle array comprising:
providing a microneedle array having a substrate and a plurality of microneedles;
providing a coating solution comprising a carrier fluid and a coating material;
providing a coating apparatus comprising a coating substrate and a supporting member for the microneedle array, wherein at least one of the coating substrate and the microneedle array is flexibly mounted within the coating apparatus;
applying the coating solution onto a first major surface of the coating substrate to form a layer of applied coating solution having a thickness equal to or less than the height of at least one of the microneedles, wherein the coating solution is applied to the first major surface of the coating substrate with a pickup plate or an extrusion die;
performing a transfer step of bringing the first major surface of the coating substrate into contact with the microneedles and removing the coating substrate from contact with the microneedles, thereby transferring at least a portion of the coating solution to the microneedle array; and
allowing the transferred carrier fluid to evaporate.

20. A method as claimed in claim 19 wherein the coating substrate is flexibly mounted.

21. A method as claimed in claim 20 wherein the coating substrate is a flexible film.

22. A method as claimed in claim 21 wherein the first major surface of the coating substrate has a leading edge and a trailing edge and wherein the trailing edge of the flexible film is brought into contact with the microneedles during the transfer step.

23. A method as claimed in claim 21 wherein the microneedle array is oriented so that the microneedles are facing upward and the coating solution on the flexible film is facing downwards when it is brought into contact with the microneedles.

24. A method as claimed in claim 19 wherein the microneedle array is flexibly mounted.

25. A method as claimed in claim 24 wherein the coating substrate is a fixed surface.

26. A method as claimed in claim 25 wherein an excess of coating solution is applied to the coating substrate and a doctoring step is performed to provide the layer of applied coating solution having a thickness equal to or less than the height of at least one of the microneedles.

27. A method as claimed in claim 24 wherein the coating substrate is flexibly mounted.

28. A method as claimed in claim 19 wherein at least a portion of the first major surface of the coating substrate is hydrophilic.

29. A method as claimed in claim 19 wherein the entire portion of the first major surface of the coating substrate is hydrophilic.

* * * * *